(12) United States Patent
O'Connor et al.

(10) Patent No.: US 11,565,043 B2
(45) Date of Patent: Jan. 31, 2023

(54) SAFETY CONSTRAINTS FOR A CONTROL ALGORITHM BASED DRUG DELIVERY SYSTEM

(71) Applicant: Insulet Corporation, Acton, MA (US)

(72) Inventors: Jason O'Connor, Acton, MA (US); Joon Bok Lee, Lowell, MA (US); Trang Ly, Concord, MA (US); Yibin Zheng, Hartland, WI (US); Thomas Arnold Peyser, Menlo Park, CA (US); Jennifer Lena Schneider, Palo Alto, CA (US)

(73) Assignee: Insulet Corporation, Acton, MA (US)

( * ) Notice: Subject to any disclaimer, the term of this patent is extended or adjusted under 35 U.S.C. 154(b) by 935 days.

(21) Appl. No.: 16/402,753

(22) Filed: May 3, 2019

(65) Prior Publication Data

US 2019/0336683 A1   Nov. 7, 2019

Related U.S. Application Data

(60) Provisional application No. 62/667,118, filed on May 4, 2018.

(51) Int. Cl.
*G08B 21/04* (2006.01)
*A61M 5/172* (2006.01)
(Continued)

(52) U.S. Cl.
CPC ....... *A61M 5/1723* (2013.01); *A61B 5/14532* (2013.01); *A61M 5/145* (2013.01);
(Continued)

(58) Field of Classification Search
USPC ... 340/539.12, 539.24, 825.22, 691.6, 691.2, 340/575, 286.07, 286.08, 825.49, 5.82,
(Continued)

(56) References Cited

U.S. PATENT DOCUMENTS 303,013 A   8/1884   Horton
2,797,149 A   6/1957   Skeggs
(Continued)

FOREIGN PATENT DOCUMENTS

AU   2015200834 A1   3/2015
AU   2015301146 A1   3/2017
(Continued)

OTHER PUBLICATIONS

US 5,954,699 A, 09/1999, Jost et al. (withdrawn)
(Continued)

*Primary Examiner* — Daniel Previl
(74) *Attorney, Agent, or Firm* — Goodwin Procter LLP

(57) ABSTRACT

Disclosed are a system, methods and computer-readable medium products that provide safety constraints for an insulin-delivery management program. Various examples provide safety constraints for a control algorithm-based drug delivery system that provides automatic delivery of a drug based on sensor input. Glucose measurement values may be received at regular time intervals from a sensor. A processor may predict future glucose values based on prior glucose measurement values. The safety constraints assist in safe operation of the drug delivery system during various operational scenarios. In some examples, predicted future glucose values may be used to implement safety constraints that mitigate under-delivery or over-delivery of the drug while not overly burdening the user of the drug delivery system and without sacrificing performance of the drug delivery system. Other safety constraints are also disclosed.

20 Claims, 13 Drawing Sheets

(51) Int. Cl.
*A61B 5/145* (2006.01)
*A61M 5/142* (2006.01)
*A61M 5/145* (2006.01)
*A61B 5/00* (2006.01)

(52) U.S. Cl.
CPC ......... *A61M 5/14244* (2013.01); *A61B 5/486* (2013.01); *A61B 5/6832* (2013.01); *A61M 2005/14208* (2013.01); *A61M 2005/14252* (2013.01); *A61M 2205/18* (2013.01); *A61M 2205/52* (2013.01); *A61M 2230/201* (2013.01)

(58) Field of Classification Search
USPC .............................................. 340/5.83, 5.52
See application file for complete search history.

(56) References Cited

U.S. PATENT DOCUMENTS

| | | |
|---|---|---|
| 3,631,847 A | 1/1972 | Hobbs |
| 3,634,039 A | 1/1972 | Brondy |
| 3,812,843 A | 5/1974 | Wootten et al. |
| 3,841,328 A | 10/1974 | Jensen |
| 3,963,380 A | 6/1976 | Thomas, Jr. et al. |
| 4,055,175 A | 10/1977 | Clemens et al. |
| 4,146,029 A | 3/1979 | Ellinwood, Jr. |
| 4,151,845 A | 5/1979 | Clemens |
| 4,245,634 A | 1/1981 | Albisser et al. |
| 4,368,980 A | 1/1983 | Aldred et al. |
| 4,373,527 A | 2/1983 | Fischell |
| 4,403,984 A | 9/1983 | Ash et al. |
| 4,464,170 A | 8/1984 | Clemens et al. |
| 4,469,481 A | 9/1984 | Kobayashi |
| 4,475,901 A | 10/1984 | Kraegen et al. |
| 4,526,568 A | 7/1985 | Clemens et al. |
| 4,526,569 A | 7/1985 | Bernardi |
| 4,529,401 A | 7/1985 | Leslie et al. |
| 4,559,033 A | 12/1985 | Stephen et al. |
| 4,559,037 A | 12/1985 | Franetzki et al. |
| 4,573,968 A | 3/1986 | Parker |
| 4,624,661 A | 11/1986 | Arimond |
| 4,633,878 A | 1/1987 | Bombardieri |
| 4,657,529 A | 4/1987 | Prince et al. |
| 4,685,903 A | 8/1987 | Cable et al. |
| 4,731,726 A | 3/1988 | Allen, III |
| 4,743,243 A | 5/1988 | Vaillancourt |
| 4,755,173 A | 7/1988 | Konopka et al. |
| 4,781,688 A | 11/1988 | Thoma et al. |
| 4,781,693 A | 11/1988 | Martinez et al. |
| 4,808,161 A | 2/1989 | Kamen |
| 4,854,170 A | 8/1989 | Brimhall et al. |
| 4,886,499 A | 12/1989 | Cirelli et al. |
| 4,900,292 A | 2/1990 | Berry et al. |
| 4,919,596 A | 4/1990 | Slate et al. |
| 4,925,444 A | 5/1990 | Orkin et al. |
| 4,940,527 A | 7/1990 | Kazlauskas et al. |
| 4,975,581 A | 12/1990 | Robinson et al. |
| 4,976,720 A | 12/1990 | Machold et al. |
| 4,981,140 A | 1/1991 | Wyatt |
| 4,994,047 A | 2/1991 | Walker et al. |
| 5,007,286 A | 4/1991 | Malcolm et al. |
| 5,097,834 A | 3/1992 | Skrabal |
| 5,102,406 A | 4/1992 | Arnold |
| 5,109,850 A | 5/1992 | Blanco et al. |
| 5,125,415 A | 6/1992 | Bell |
| 5,134,079 A | 7/1992 | Cusack et al. |
| 5,153,827 A | 10/1992 | Coutre et al. |
| 5,165,406 A | 11/1992 | Wong |
| 5,176,662 A | 1/1993 | Bartholomew et al. |
| 5,178,609 A | 1/1993 | Ishikawa |
| 5,207,642 A | 5/1993 | Orkin et al. |
| 5,232,439 A | 8/1993 | Campbell et al. |
| 5,237,993 A | 8/1993 | Skrabal |
| 5,244,463 A | 9/1993 | Cordner, Jr. et al. |
| 5,257,980 A | 11/1993 | Van Antwerp et al. |
| 5,273,517 A | 12/1993 | Barone et al. |
| 5,281,808 A | 1/1994 | Kunkel |
| 5,299,571 A | 4/1994 | Mastrototaro |
| 5,308,982 A | 5/1994 | Ivaldi et al. |
| 5,342,298 A | 8/1994 | Michaels et al. |
| 5,377,674 A | 1/1995 | Kuestner |
| 5,380,665 A | 1/1995 | Cusack et al. |
| 5,385,539 A | 1/1995 | Maynard |
| 5,389,078 A | 2/1995 | Zalesky et al. |
| 5,411,889 A | 5/1995 | Hoots et al. |
| 5,421,812 A | 6/1995 | Langley et al. |
| 5,468,727 A | 11/1995 | Phillips et al. |
| 5,505,709 A | 4/1996 | Funderburk et al. |
| 5,505,828 A | 4/1996 | Wong et al. |
| 5,507,288 A | 4/1996 | Bocker et al. |
| 5,533,389 A | 7/1996 | Kamen et al. |
| 5,558,640 A | 9/1996 | Pfeiler et al. |
| 5,569,186 A | 10/1996 | Lord et al. |
| 5,584,813 A | 12/1996 | Livingston et al. |
| 5,609,572 A | 3/1997 | Lang |
| 5,665,065 A | 9/1997 | Colman et al. |
| 5,678,539 A | 10/1997 | Schubert et al. |
| 5,685,844 A | 11/1997 | Marttila |
| 5,685,859 A | 11/1997 | Kornerup |
| 5,693,018 A | 12/1997 | Kriesel et al. |
| 5,697,899 A | 12/1997 | Hillman et al. |
| 5,700,695 A | 12/1997 | Yassinzadeh et al. |
| 5,703,364 A | 12/1997 | Rosenthal |
| 5,714,123 A | 2/1998 | Sohrab |
| 5,716,343 A | 2/1998 | Kriesel et al. |
| 5,722,397 A | 3/1998 | Eppstein |
| 5,741,228 A | 4/1998 | Lambrecht et al. |
| 5,746,217 A | 5/1998 | Erickson et al. |
| 5,755,682 A | 5/1998 | Knudson et al. |
| 5,758,643 A | 6/1998 | Wong et al. |
| 5,800,405 A | 9/1998 | McPhee |
| 5,800,420 A | 9/1998 | Gross et al. |
| 5,801,057 A | 9/1998 | Smart et al. |
| 5,804,048 A | 9/1998 | Wong et al. |
| 5,817,007 A | 10/1998 | Fodgaard et al. |
| 5,820,622 A | 10/1998 | Gross et al. |
| 5,823,951 A | 10/1998 | Messerschmidt |
| 5,840,020 A | 11/1998 | Heinonen et al. |
| 5,848,991 A | 12/1998 | Gross et al. |
| 5,851,197 A | 12/1998 | Marano et al. |
| 5,858,005 A | 1/1999 | Kriesel |
| 5,865,806 A | 2/1999 | Howell |
| 5,871,470 A | 2/1999 | McWha |
| 5,879,310 A | 3/1999 | Sopp et al. |
| 5,902,253 A | 5/1999 | Pfeiffer et al. |
| 5,931,814 A | 8/1999 | Alex et al. |
| 5,932,175 A | 8/1999 | Knute et al. |
| 5,935,099 A | 8/1999 | Peterson et al. |
| 5,947,911 A | 9/1999 | Wong et al. |
| 5,971,941 A | 10/1999 | Simons et al. |
| 5,993,423 A | 11/1999 | Choi |
| 5,997,501 A | 12/1999 | Gross et al. |
| 6,017,318 A | 1/2000 | Gauthier et al. |
| 6,024,539 A | 2/2000 | Blomquist |
| 6,032,059 A | 2/2000 | Henning et al. |
| 6,036,924 A | 3/2000 | Simons et al. |
| 6,040,578 A | 3/2000 | Malin et al. |
| 6,049,727 A | 4/2000 | Grothall |
| 6,050,978 A | 4/2000 | Or et al. |
| 6,058,934 A | 5/2000 | Sullivan |
| 6,066,103 A | 5/2000 | Duchon et al. |
| 6,071,292 A | 6/2000 | Makower et al. |
| 6,072,180 A | 6/2000 | Kramer et al. |
| 6,077,055 A | 6/2000 | Vilks |
| 6,090,092 A | 7/2000 | Fowles et al. |
| 6,101,406 A | 8/2000 | Hacker et al. |
| 6,102,872 A | 8/2000 | Doneen et al. |
| 6,115,673 A | 9/2000 | Malin et al. |
| 6,123,827 A | 9/2000 | Wong et al. |
| 6,124,134 A | 9/2000 | Stark |
| 6,126,637 A | 10/2000 | Kriesel et al. |
| 6,128,519 A | 10/2000 | Say |
| 6,142,939 A | 11/2000 | Eppstein et al. |
| 6,143,164 A | 11/2000 | Heller et al. |
| 6,157,041 A | 12/2000 | Thomas et al. |

(56) References Cited

U.S. PATENT DOCUMENTS

| | | | |
|---|---|---|---|
| 6,161,028 A | 12/2000 | Braig et al. |
| 6,162,639 A | 12/2000 | Douglas |
| 6,196,046 B1 | 3/2001 | Braig et al. |
| 6,200,287 B1 | 3/2001 | Keller et al. |
| 6,200,338 B1 | 3/2001 | Solomon et al. |
| 6,214,629 B1 | 4/2001 | Freitag et al. |
| 6,226,082 B1 | 5/2001 | Roe |
| 6,244,776 B1 | 6/2001 | Wiley |
| 6,261,065 B1 | 7/2001 | Nayak et al. |
| 6,262,798 B1 | 7/2001 | Shepherd et al. |
| 6,270,455 B1 | 8/2001 | Brown |
| 6,271,045 B1 | 8/2001 | Douglas et al. |
| 6,280,381 B1 | 8/2001 | Malin et al. |
| 6,285,448 B1 | 9/2001 | Kuenstner |
| 6,309,370 B1 | 10/2001 | Haim et al. |
| 6,312,888 B1 | 11/2001 | Wong et al. |
| 6,334,851 B1 | 1/2002 | Hayes et al. |
| 6,375,627 B1 | 4/2002 | Mauze et al. |
| 6,379,301 B1 | 4/2002 | Worthington et al. |
| 6,402,689 B1 | 6/2002 | Scarantino et al. |
| 6,470,279 B1 | 10/2002 | Samsoondar |
| 6,475,196 B1 | 11/2002 | Vachon |
| 6,477,901 B1 | 11/2002 | Tadigadapa et al. |
| 6,484,044 B1 | 11/2002 | Lilienfeld-Toal |
| 6,491,656 B1 | 12/2002 | Morris |
| 6,512,937 B2 | 1/2003 | Blank et al. |
| 6,525,509 B1 | 2/2003 | Petersson et al. |
| 6,528,809 B1 | 3/2003 | Thomas et al. |
| 6,540,672 B1 | 4/2003 | Simonsen et al. |
| 6,544,212 B2 | 4/2003 | Galley et al. |
| 6,546,268 B1 | 4/2003 | Ishikawa et al. |
| 6,546,269 B1 | 4/2003 | Kurnik |
| 6,553,841 B1 | 4/2003 | Blouch |
| 6,554,798 B1 | 4/2003 | Mann et al. |
| 6,556,850 B1 | 4/2003 | Braig et al. |
| 6,558,351 B1 | 5/2003 | Steil et al. |
| 6,560,471 B1 | 5/2003 | Heller et al. |
| 6,561,978 B1 | 5/2003 | Conn et al. |
| 6,562,001 B2 | 5/2003 | Lebel et al. |
| 6,562,014 B2 | 5/2003 | Lin et al. |
| 6,569,125 B2 | 5/2003 | Jepson et al. |
| 6,572,542 B1 | 6/2003 | Houben et al. |
| 6,572,545 B2 | 6/2003 | Knobbe et al. |
| 6,574,490 B2 | 6/2003 | Abbink et al. |
| 6,575,905 B2 | 6/2003 | Knobbe et al. |
| 6,580,934 B1 | 6/2003 | Braig et al. |
| 6,618,603 B2 | 9/2003 | Varalli et al. |
| 6,633,772 B2 | 10/2003 | Ford et al. |
| 6,645,142 B2 | 11/2003 | Braig et al. |
| 6,653,091 B1 | 11/2003 | Dunn et al. |
| 6,662,030 B2 | 12/2003 | Khalil et al. |
| 6,669,663 B1 | 12/2003 | Thompson |
| 6,678,542 B2 | 1/2004 | Braig et al. |
| 6,699,221 B2 | 3/2004 | Vaillancourt |
| 6,718,189 B2 | 4/2004 | Rohrscheib et al. |
| 6,721,582 B2 | 4/2004 | Trepagnier et al. |
| 6,728,560 B2 | 4/2004 | Kollias et al. |
| 6,740,059 B2 | 5/2004 | Flaherty |
| 6,740,072 B2 | 5/2004 | Starkweather et al. |
| 6,751,490 B2 | 6/2004 | Esenaliev et al. |
| 6,758,835 B2 | 7/2004 | Close et al. |
| 6,780,156 B2 | 8/2004 | Haueter et al. |
| 6,810,290 B2 | 10/2004 | Lebel et al. |
| 6,837,858 B2 | 1/2005 | Cunningham et al. |
| 6,837,988 B2 | 1/2005 | Leong et al. |
| 6,846,288 B2 | 1/2005 | Nagar et al. |
| 6,862,534 B2 | 3/2005 | Sterling et al. |
| 6,865,408 B1 | 3/2005 | Abbink et al. |
| 6,890,291 B2 | 5/2005 | Robinson et al. |
| 6,936,029 B2 | 8/2005 | Mann et al. |
| 6,949,081 B1 | 9/2005 | Chance |
| 6,958,809 B2 | 10/2005 | Sterling et al. |
| 6,989,891 B2 | 1/2006 | Braig et al. |
| 6,990,366 B2 | 1/2006 | Say et al. |
| 7,008,404 B2 | 3/2006 | Nakajima |
| 7,009,180 B2 | 3/2006 | Sterling et al. |
| 7,016,713 B2 | 3/2006 | Gardner et al. |
| 7,018,360 B2 | 3/2006 | Flaherty et al. |
| 7,025,743 B2 | 4/2006 | Mann et al. |
| 7,025,744 B2 | 4/2006 | Utterberg et al. |
| 7,027,848 B2 | 4/2006 | Robinson et al. |
| 7,043,288 B2 | 5/2006 | Davis, III et al. |
| 7,060,059 B2 | 6/2006 | Keith et al. |
| 7,061,593 B2 | 6/2006 | Braig et al. |
| 7,096,124 B2 | 8/2006 | Sterling et al. |
| 7,115,205 B2 | 10/2006 | Robinson et al. |
| 7,128,727 B2 | 10/2006 | Flaherty et al. |
| 7,139,593 B2 | 11/2006 | Kavak et al. |
| 7,139,598 B2 | 11/2006 | Hull et al. |
| 7,144,384 B2 | 12/2006 | Gorman et al. |
| 7,171,252 B1 | 1/2007 | Scarantino et al. |
| 7,190,988 B2 | 3/2007 | Say et al. |
| 7,204,823 B2 | 4/2007 | Estes et al. |
| 7,248,912 B2 | 7/2007 | Gough et al. |
| 7,267,665 B2 | 9/2007 | Steil et al. |
| 7,271,912 B2 | 9/2007 | Sterling et al. |
| 7,278,983 B2 | 10/2007 | Ireland et al. |
| 7,291,107 B2 | 11/2007 | Hellwig et al. |
| 7,291,497 B2 | 11/2007 | Holmes et al. |
| 7,303,549 B2 | 12/2007 | Flaherty et al. |
| 7,303,622 B2 | 12/2007 | Loch et al. |
| 7,303,922 B2 | 12/2007 | Jeng et al. |
| 7,354,420 B2 | 4/2008 | Steil et al. |
| 7,388,202 B2 | 6/2008 | Sterling et al. |
| 7,402,153 B2 | 7/2008 | Steil et al. |
| 7,404,796 B2 | 7/2008 | Ginsberg |
| 7,429,255 B2 | 9/2008 | Thompson |
| 7,460,130 B2 | 12/2008 | Salganicoff |
| 7,481,787 B2 | 1/2009 | Gable et al. |
| 7,491,187 B2 | 2/2009 | Van Den Berghe et al. |
| 7,500,949 B2 | 3/2009 | Gottlieb et al. |
| 7,509,156 B2 | 3/2009 | Flanders |
| 7,547,281 B2 | 6/2009 | Hayes et al. |
| 7,569,030 B2 | 8/2009 | Lebel et al. |
| 7,608,042 B2 | 10/2009 | Goldberger et al. |
| 7,651,845 B2 | 1/2010 | Doyle, III et al. |
| 7,680,529 B2 | 3/2010 | Kroll |
| 7,734,323 B2 | 6/2010 | Blomquist et al. |
| 7,766,829 B2 | 8/2010 | Sloan et al. |
| 7,785,258 B2 | 8/2010 | Braig et al. |
| 7,806,854 B2 | 10/2010 | Damiano et al. |
| 7,806,886 B2 | 10/2010 | Kanderian, Jr. et al. |
| 7,918,825 B2 | 4/2011 | DConnor et al. |
| 7,946,985 B2 | 5/2011 | Mastrototaro et al. |
| 7,972,296 B2 | 7/2011 | Braig et al. |
| 8,221,345 B2 | 7/2012 | Blomquist |
| 8,251,907 B2 | 8/2012 | Sterling et al. |
| 8,449,524 B2 | 5/2013 | Braig et al. |
| 8,452,359 B2 | 5/2013 | Rebec et al. |
| 8,454,576 B2 | 6/2013 | Mastrototaro et al. |
| 8,467,980 B2 * | 6/2013 | Campbell ......... A61M 5/14244 702/50 |
| 8,478,557 B2 | 7/2013 | Hayter et al. |
| 8,547,239 B2 | 10/2013 | Peatfield et al. |
| 8,597,274 B2 | 12/2013 | Sloan et al. |
| 8,622,988 B2 | 1/2014 | Hayter |
| 8,810,394 B2 | 8/2014 | Kalpin |
| 9,061,097 B2 | 6/2015 | Holt et al. |
| 9,171,343 B1 | 10/2015 | Fischell et al. |
| 9,233,204 B2 * | 1/2016 | Booth .................. G16H 10/40 |
| 9,486,571 B2 | 11/2016 | Rosinko |
| 9,486,580 B2 * | 11/2016 | Booth .................. A61B 5/4839 |
| 9,579,456 B2 | 2/2017 | Budiman et al. |
| 9,743,224 B2 | 8/2017 | San Vicente et al. |
| 9,907,515 B2 | 3/2018 | Doyle, III et al. |
| 9,980,140 B1 | 5/2018 | Spencer et al. |
| 9,984,773 B2 | 5/2018 | Gondhalekar et al. |
| 10,248,839 B2 | 4/2019 | Levy et al. |
| 10,335,464 B1 | 7/2019 | Michelich et al. |
| 10,583,250 B2 | 3/2020 | Mazlish et al. |
| 10,737,024 B2 | 8/2020 | Schmid |
| 10,987,468 B2 | 4/2021 | Mazlish et al. |
| 11,197,964 B2 * | 12/2021 | Sjolund ............... A61B 5/0022 |
| 11,260,169 B2 * | 3/2022 | Estes ................. A61M 5/14244 |

(56) References Cited

U.S. PATENT DOCUMENTS

| | | |
|---|---|---|
| 2001/0021803 A1 | 9/2001 | Blank et al. |
| 2001/0034023 A1 | 10/2001 | Stanton, Jr. et al. |
| 2001/0034502 A1 | 10/2001 | Moberg et al. |
| 2001/0051377 A1 | 12/2001 | Hammer et al. |
| 2001/0053895 A1 | 12/2001 | Vaillancourt |
| 2002/0010401 A1 | 1/2002 | Bushmakin et al. |
| 2002/0010423 A1 | 1/2002 | Gross et al. |
| 2002/0016568 A1 | 2/2002 | Lebel et al. |
| 2002/0040208 A1 | 4/2002 | Flaherty et al. |
| 2002/0123740 A1 | 9/2002 | Flaherty et al. |
| 2002/0128543 A1 | 9/2002 | Leonhardt |
| 2002/0147423 A1 | 10/2002 | Burbank et al. |
| 2002/0155425 A1 | 10/2002 | Han et al. |
| 2002/0161288 A1 | 10/2002 | Shin et al. |
| 2003/0023148 A1 | 1/2003 | Lorenz et al. |
| 2003/0050621 A1 | 3/2003 | Lebel et al. |
| 2003/0060692 A1 | 3/2003 | Ruchti et al. |
| 2003/0086074 A1 | 5/2003 | Braig et al. |
| 2003/0086075 A1 | 5/2003 | Braig et al. |
| 2003/0090649 A1 | 5/2003 | Sterling et al. |
| 2003/0100040 A1 | 5/2003 | Bonnecaze et al. |
| 2003/0130616 A1 | 7/2003 | Steil et al. |
| 2003/0135388 A1 | 7/2003 | Martucci et al. |
| 2003/0144582 A1 | 7/2003 | Cohen et al. |
| 2003/0163097 A1 | 8/2003 | Fleury et al. |
| 2003/0195404 A1 | 10/2003 | Knobbe et al. |
| 2003/0208113 A1 | 11/2003 | Mault et al. |
| 2003/0208154 A1 | 11/2003 | Close et al. |
| 2003/0212379 A1 | 11/2003 | Bylund et al. |
| 2003/0216627 A1 | 11/2003 | Lorenz et al. |
| 2003/0220605 A1 | 11/2003 | Bowman, Jr. et al. |
| 2004/0010207 A1 | 1/2004 | Flaherty et al. |
| 2004/0034295 A1 | 2/2004 | Salganicoff |
| 2004/0045879 A1 | 3/2004 | Shults et al. |
| 2004/0051368 A1 | 3/2004 | Caputo et al. |
| 2004/0064259 A1 | 4/2004 | Haaland et al. |
| 2004/0097796 A1 | 5/2004 | Berman et al. |
| 2004/0116847 A1 | 6/2004 | Wall |
| 2004/0122353 A1 | 6/2004 | Shahmirian et al. |
| 2004/0133166 A1 | 7/2004 | Moberg et al. |
| 2004/0147034 A1 | 7/2004 | Gore et al. |
| 2004/0171983 A1 | 9/2004 | Sparks et al. |
| 2004/0203357 A1 | 10/2004 | Nassimi |
| 2004/0204868 A1 | 10/2004 | Maynard et al. |
| 2004/0215492 A1 | 10/2004 | Choi |
| 2004/0220517 A1 | 11/2004 | Starkweather et al. |
| 2004/0241736 A1 | 12/2004 | Hendee et al. |
| 2004/0249308 A1 | 12/2004 | Forssell |
| 2005/0003470 A1 | 1/2005 | Nelson et al. |
| 2005/0020980 A1 | 1/2005 | Inoue et al. |
| 2005/0022274 A1 | 1/2005 | Campbell et al. |
| 2005/0033148 A1 | 2/2005 | Haueter et al. |
| 2005/0049179 A1 | 3/2005 | Davidson et al. |
| 2005/0065464 A1 | 3/2005 | Talbot et al. |
| 2005/0065465 A1 | 3/2005 | Lebel et al. |
| 2005/0075624 A1 | 4/2005 | Miesel |
| 2005/0105095 A1 | 5/2005 | Pesach et al. |
| 2005/0137573 A1 | 6/2005 | McLaughlin |
| 2005/0171503 A1 | 8/2005 | Van Den Berghe et al. |
| 2005/0182306 A1 | 8/2005 | Sloan |
| 2005/0192494 A1 | 9/2005 | Ginsberg |
| 2005/0192557 A1 | 9/2005 | Brauker et al. |
| 2005/0197621 A1 | 9/2005 | Poulsen et al. |
| 2005/0203360 A1 | 9/2005 | Brauker et al. |
| 2005/0203461 A1 | 9/2005 | Flaherty et al. |
| 2005/0238507 A1 | 10/2005 | Dilanni et al. |
| 2005/0261660 A1 | 11/2005 | Choi |
| 2005/0272640 A1 | 12/2005 | Doyle, III et al. |
| 2005/0277912 A1 | 12/2005 | John |
| 2006/0009727 A1 | 1/2006 | OMahony et al. |
| 2006/0079809 A1 | 4/2006 | Goldberger et al. |
| 2006/0100494 A1 | 5/2006 | Kroll |
| 2006/0134323 A1 | 6/2006 | OBrien |
| 2006/0167350 A1 | 7/2006 | Monfre et al. |
| 2006/0173406 A1 | 8/2006 | Hayes et al. |
| 2006/0189925 A1 | 8/2006 | Gable et al. |
| 2006/0189926 A1 | 8/2006 | Hall et al. |
| 2006/0197015 A1 | 9/2006 | Sterling et al. |
| 2006/0200070 A1 | 9/2006 | Callicoat et al. |
| 2006/0204535 A1 | 9/2006 | Johnson |
| 2006/0229531 A1 | 10/2006 | Goldberger et al. |
| 2006/0253085 A1 | 11/2006 | Geismar et al. |
| 2006/0264895 A1 | 11/2006 | Flanders |
| 2006/0270983 A1 | 11/2006 | Lord et al. |
| 2006/0276771 A1 | 12/2006 | Galley et al. |
| 2006/0282290 A1 | 12/2006 | Flaherty et al. |
| 2007/0016127 A1 | 1/2007 | Staib et al. |
| 2007/0060796 A1 | 3/2007 | Kim |
| 2007/0060869 A1 | 3/2007 | Tolle et al. |
| 2007/0060872 A1 | 3/2007 | Hall et al. |
| 2007/0083160 A1 | 4/2007 | Hall et al. |
| 2007/0106135 A1 | 5/2007 | Sloan et al. |
| 2007/0116601 A1 | 5/2007 | Patton |
| 2007/0118405 A1 | 5/2007 | Campbell et al. |
| 2007/0129690 A1 | 6/2007 | Rosenblatt et al. |
| 2007/0142720 A1 | 6/2007 | Ridder et al. |
| 2007/0173761 A1 | 7/2007 | Kanderian et al. |
| 2007/0173974 A1 | 7/2007 | Lin |
| 2007/0179352 A1 | 8/2007 | Randlov et al. |
| 2007/0191716 A1 | 8/2007 | Goldberger et al. |
| 2007/0197163 A1 | 8/2007 | Robertson |
| 2007/0225675 A1 | 9/2007 | Robinson et al. |
| 2007/0244381 A1 | 10/2007 | Robinson et al. |
| 2007/0249007 A1 | 10/2007 | Rosero |
| 2007/0264707 A1 | 11/2007 | Liederman et al. |
| 2007/0282269 A1 | 12/2007 | Carter et al. |
| 2007/0287985 A1 | 12/2007 | Estes et al. |
| 2007/0293843 A1 | 12/2007 | Ireland et al. |
| 2008/0033272 A1 | 2/2008 | Gough et al. |
| 2008/0051764 A1 | 2/2008 | Dent et al. |
| 2008/0058625 A1 | 3/2008 | McGarraugh et al. |
| 2008/0065050 A1 | 3/2008 | Sparks et al. |
| 2008/0071157 A1 | 3/2008 | McGarraugh et al. |
| 2008/0071158 A1 | 3/2008 | McGarraugh et al. |
| 2008/0078400 A1 | 4/2008 | Martens et al. |
| 2008/0097289 A1 | 4/2008 | Steil et al. |
| 2008/0132880 A1 | 6/2008 | Buchman |
| 2008/0161664 A1 | 7/2008 | Mastrototaro et al. |
| 2008/0172026 A1 | 7/2008 | Blomquist |
| 2008/0177165 A1 | 7/2008 | Blomquist et al. |
| 2008/0188796 A1 | 8/2008 | Steil et al. |
| 2008/0200838 A1 | 8/2008 | Goldberger et al. |
| 2008/0206067 A1 | 8/2008 | De Corral et al. |
| 2008/0208113 A1 | 8/2008 | Damiano et al. |
| 2008/0214919 A1 | 9/2008 | Harmon et al. |
| 2008/0228056 A1 | 9/2008 | Blomquist et al. |
| 2008/0249386 A1 | 10/2008 | Besterman et al. |
| 2008/0269585 A1 | 10/2008 | Ginsberg |
| 2008/0269714 A1 | 10/2008 | Mastrototaro et al. |
| 2008/0269723 A1 | 10/2008 | Mastrototaro et al. |
| 2008/0287906 A1 | 11/2008 | Burkholz et al. |
| 2009/0006061 A1 | 1/2009 | Thukral et al. |
| 2009/0018406 A1 | 1/2009 | Yodfat et al. |
| 2009/0030398 A1 | 1/2009 | Yodfat et al. |
| 2009/0036753 A1 | 2/2009 | King |
| 2009/0043240 A1 | 2/2009 | Robinson et al. |
| 2009/0054753 A1* | 2/2009 | Robinson .............. G16H 40/63 422/68.1 |
| 2009/0069743 A1 | 3/2009 | Krishnamoorthy et al. |
| 2009/0069745 A1 | 3/2009 | Estes et al. |
| 2009/0069787 A1 | 3/2009 | Estes et al. |
| 2009/0099521 A1 | 4/2009 | Gravesen et al. |
| 2009/0105573 A1 | 4/2009 | Malecha |
| 2009/0131861 A1 | 5/2009 | Braig et al. |
| 2009/0156922 A1 | 6/2009 | Goldberger et al. |
| 2009/0156924 A1 | 6/2009 | Shariati et al. |
| 2009/0163781 A1 | 6/2009 | Say et al. |
| 2009/0198350 A1 | 8/2009 | Thiele |
| 2009/0221890 A1 | 9/2009 | Saffer et al. |
| 2009/0228214 A1 | 9/2009 | Say et al. |
| 2009/0318791 A1 | 12/2009 | Kaastrup |
| 2009/0326343 A1 | 12/2009 | Gable et al. |
| 2010/0057042 A1 | 3/2010 | Hayter |
| 2010/0114026 A1 | 5/2010 | Karratt et al. |

(56) References Cited

U.S. PATENT DOCUMENTS

| | | |
|---|---|---|
| 2010/0121170 A1 | 5/2010 | Rule |
| 2010/0137784 A1 | 6/2010 | Cefai et al. |
| 2010/0152658 A1 | 6/2010 | Hanson et al. |
| 2010/0174228 A1 | 7/2010 | Buckingham et al. |
| 2010/0211003 A1 | 8/2010 | Sundar et al. |
| 2010/0228110 A1 | 9/2010 | Tsoukalis |
| 2010/0262117 A1 | 10/2010 | Magni et al. |
| 2010/0262434 A1 | 10/2010 | Shaya |
| 2010/0295686 A1 | 11/2010 | Sloan et al. |
| 2010/0298765 A1 | 11/2010 | Budiman et al. |
| 2011/0021584 A1 | 1/2011 | Berggren et al. |
| 2011/0028817 A1 | 2/2011 | Jin et al. |
| 2011/0054390 A1 | 3/2011 | Searle et al. |
| 2011/0054399 A1 | 3/2011 | Chong et al. |
| 2011/0124996 A1 | 5/2011 | Reinke et al. |
| 2011/0144586 A1 | 6/2011 | Michaud et al. |
| 2011/0160652 A1 | 6/2011 | Yodat et al. |
| 2011/0178472 A1 | 7/2011 | Cabiri |
| 2011/0190694 A1 | 8/2011 | Lanier, Jr. et al. |
| 2011/0202005 A1 | 8/2011 | Yodat et al. |
| 2011/0218495 A1 | 9/2011 | Remde |
| 2011/0230833 A1 | 9/2011 | Landman et al. |
| 2011/0251509 A1 | 10/2011 | Beyhan et al. |
| 2011/0313680 A1 | 12/2011 | Doyle et al. |
| 2011/0316562 A1 | 12/2011 | Cefai et al. |
| 2012/0003935 A1 | 1/2012 | Lydon et al. |
| 2012/0010594 A1 | 1/2012 | Holt et al. |
| 2012/0030393 A1 | 2/2012 | Ganesh et al. |
| 2012/0053556 A1 | 3/2012 | Lee |
| 2012/0078067 A1 | 3/2012 | Kovatchev et al. |
| 2012/0078161 A1 | 3/2012 | Masterson et al. |
| 2012/0078181 A1 | 3/2012 | Smith et al. |
| 2012/0101451 A1 | 4/2012 | Boit et al. |
| 2012/0123234 A1 | 5/2012 | Atlas et al. |
| 2012/0136336 A1 | 5/2012 | Mastrototaro et al. |
| 2012/0190955 A1 | 7/2012 | Rao et al. |
| 2012/0203085 A1 | 8/2012 | Rebec |
| 2012/0203178 A1 | 8/2012 | Tverskoy |
| 2012/0215087 A1 | 8/2012 | Cobelli et al. |
| 2012/0225134 A1 | 9/2012 | Komorowski |
| 2012/0226259 A1 | 9/2012 | Yodfat et al. |
| 2012/0232520 A1 | 9/2012 | Sloan et al. |
| 2012/0238851 A1 | 9/2012 | Kamen et al. |
| 2012/0271655 A1 | 10/2012 | Knobel et al. |
| 2012/0277668 A1 | 11/2012 | Chawla |
| 2012/0282111 A1 | 11/2012 | Nip et al. |
| 2012/0295550 A1 | 11/2012 | Wilson et al. |
| 2013/0030358 A1 | 1/2013 | Yodfat et al. |
| 2013/0158503 A1 | 6/2013 | Kanderian, Jr. et al. |
| 2013/0178791 A1 | 7/2013 | Javitt |
| 2013/0231642 A1 | 9/2013 | Doyle et al. |
| 2013/0253472 A1 | 9/2013 | Cabiri |
| 2013/0261406 A1 | 10/2013 | Rebec et al. |
| 2013/0296823 A1 | 11/2013 | Melker et al. |
| 2013/0317753 A1 | 11/2013 | Kamen et al. |
| 2013/0338576 A1 | 12/2013 | OConnor et al. |
| 2014/0005633 A1 | 1/2014 | Finan |
| 2014/0066886 A1 | 3/2014 | Roy et al. |
| 2014/0074033 A1 | 3/2014 | Sonderegger et al. |
| 2014/0121635 A1 | 5/2014 | Hayter |
| 2014/0128839 A1 | 5/2014 | Dilanni et al. |
| 2014/0135880 A1 | 5/2014 | Baumgartner et al. |
| 2014/0146202 A1 | 5/2014 | Boss et al. |
| 2014/0180203 A1 | 6/2014 | Budiman et al. |
| 2014/0180240 A1* | 6/2014 | Finan .................. G16H 20/17 604/504 |
| 2014/0200426 A1 | 7/2014 | Taub et al. |
| 2014/0200559 A1 | 7/2014 | Doyle et al. |
| 2014/0230021 A1 | 8/2014 | Birtwhistle et al. |
| 2014/0276554 A1 | 9/2014 | Finan et al. |
| 2014/0276556 A1 | 9/2014 | Saint et al. |
| 2014/0278123 A1 | 9/2014 | Prodhom et al. |
| 2014/0309615 A1 | 10/2014 | Mazlish |
| 2014/0316379 A1 | 10/2014 | Sonderegger et al. |
| 2014/0325065 A1 | 10/2014 | Birtwhistle et al. |
| 2015/0018633 A1 | 1/2015 | Kovachev et al. |
| 2015/0025329 A1 | 1/2015 | Amarasingham et al. |
| 2015/0025495 A1 | 1/2015 | Peyser |
| 2015/0120317 A1 | 4/2015 | Mayou et al. |
| 2015/0134265 A1 | 5/2015 | Kohlbrecher et al. |
| 2015/0165119 A1 | 6/2015 | Palerm et al. |
| 2015/0173674 A1 | 6/2015 | Hayes et al. |
| 2015/0213217 A1 | 7/2015 | Amarasingham et al. |
| 2015/0217052 A1 | 8/2015 | Keenan et al. |
| 2015/0217053 A1 | 8/2015 | Booth et al. |
| 2015/0265767 A1 | 9/2015 | Vazquez et al. |
| 2015/0306314 A1 | 10/2015 | Doyle et al. |
| 2015/0351671 A1 | 12/2015 | Vanslyke et al. |
| 2015/0366945 A1 | 12/2015 | Greene |
| 2016/0015891 A1 | 1/2016 | Papiorek |
| 2016/0038673 A1 | 2/2016 | Morales |
| 2016/0038689 A1 | 2/2016 | Lee et al. |
| 2016/0051749 A1 | 2/2016 | Istoc |
| 2016/0082187 A1 | 3/2016 | Schaible et al. |
| 2016/0089494 A1 | 3/2016 | Guerrini |
| 2016/0175520 A1 | 6/2016 | Palerm et al. |
| 2016/0228641 A1 | 8/2016 | Gescheit et al. |
| 2016/0243318 A1 | 8/2016 | Despa et al. |
| 2016/0256087 A1 | 9/2016 | Doyle et al. |
| 2016/0287512 A1 | 10/2016 | Cooper et al. |
| 2016/0302054 A1 | 10/2016 | Kimura et al. |
| 2016/0331310 A1 | 11/2016 | Kovatchev |
| 2016/0354543 A1 | 12/2016 | Cinar et al. |
| 2017/0049386 A1 | 2/2017 | Abraham et al. |
| 2017/0143899 A1 | 5/2017 | Gondhalekar et al. |
| 2017/0143900 A1 | 5/2017 | Rioux et al. |
| 2017/0156682 A1 | 6/2017 | Doyle et al. |
| 2017/0173261 A1 | 6/2017 | OConnor et al. |
| 2017/0189625 A1 | 7/2017 | Cirillo et al. |
| 2017/0281877 A1 | 10/2017 | Marlin et al. |
| 2017/0296746 A1 | 10/2017 | Chen et al. |
| 2017/0311903 A1 | 11/2017 | Davis et al. |
| 2017/0348482 A1* | 12/2017 | Duke .................. A61M 5/1723 |
| 2018/0036495 A1 | 2/2018 | Searle et al. |
| 2018/0040255 A1 | 2/2018 | Freeman et al. |
| 2018/0075200 A1 | 3/2018 | Davis et al. |
| 2018/0075201 A1 | 3/2018 | Davis et al. |
| 2018/0075202 A1 | 3/2018 | Davis et al. |
| 2018/0092576 A1 | 4/2018 | Ambrosio |
| 2018/0126073 A1 | 5/2018 | Wu et al. |
| 2018/0169334 A1 | 6/2018 | Grosman et al. |
| 2018/0200434 A1 | 7/2018 | Mazlish et al. |
| 2018/0200438 A1 | 7/2018 | Mazlish et al. |
| 2018/0200441 A1* | 7/2018 | Desborough ...... A61B 5/14532 |
| 2018/0204636 A1 | 7/2018 | Edwards et al. |
| 2018/0277253 A1 | 9/2018 | Gondhalekar et al. |
| 2018/0289891 A1 | 10/2018 | Finan et al. |
| 2018/0296757 A1 | 10/2018 | Finan et al. |
| 2018/0342317 A1 | 11/2018 | Skirble et al. |
| 2018/0369479 A1 | 12/2018 | Hayter et al. |
| 2019/0076600 A1 | 3/2019 | Grosman et al. |
| 2019/0240403 A1 | 8/2019 | Palerm et al. |
| 2019/0290844 A1 | 9/2019 | Monirabbasi et al. |
| 2019/0336683 A1 | 11/2019 | O'Connor et al. |
| 2019/0336684 A1 | 11/2019 | OConnor et al. |
| 2019/0348157 A1 | 11/2019 | Booth et al. |
| 2020/0046268 A1 | 2/2020 | Patek et al. |
| 2020/0101222 A1 | 4/2020 | Lintereur et al. |
| 2020/0101223 A1 | 4/2020 | Lintereur et al. |
| 2020/0101225 A1 | 4/2020 | OConnor et al. |
| 2020/0219625 A1 | 7/2020 | Kahlbaugh |
| 2020/0342974 A1 | 10/2020 | Chen et al. |
| 2021/0050085 A1 | 2/2021 | Hayter et al. |
| 2021/0098105 A1 | 4/2021 | Lee et al. |
| 2022/0023536 A1 | 1/2022 | Graham et al. |

FOREIGN PATENT DOCUMENTS

| | | |
|---|---|---|
| CN | 1297140 A | 5/2001 |
| DE | 19756872 A1 | 7/1999 |
| EP | 0341049 A2 | 11/1989 |
| EP | 0496305 A2 | 7/1992 |
| EP | 0549341 A1 | 6/1993 |
| EP | 1491144 A1 | 12/2004 |

(56) References Cited

FOREIGN PATENT DOCUMENTS

| | | |
|---|---|---|
| EP | 1571582 A2 | 9/2005 |
| EP | 0801578 B1 | 7/2006 |
| EP | 2666520 A1 | 10/2009 |
| EP | 2139382 A1 | 1/2010 |
| EP | 2397181 A1 | 12/2011 |
| EP | 2695573 A2 | 2/2014 |
| EP | 2830499 A1 | 2/2015 |
| EP | 2943149 A1 | 11/2015 |
| EP | 3177344 A1 | 6/2017 |
| EP | 3314548 A1 | 5/2018 |
| EP | 2897071 B1 | 5/2019 |
| EP | 3607985 A1 | 2/2020 |
| GB | 2443261 A | 4/2008 |
| JP | 51125993 A | 11/1976 |
| JP | 02131777 A1 | 5/1990 |
| JP | 2004283378 A | 10/2004 |
| JP | 2017525451 A | 9/2017 |
| JP | 2018153569 A | 10/2018 |
| JP | 2019525276 A | 9/2019 |
| TW | 200740148 A | 10/2007 |
| TW | M452390 U | 5/2013 |
| WO | 9800193 A1 | 1/1998 |
| WO | 9956803 A1 | 11/1999 |
| WO | 0030705 A1 | 6/2000 |
| WO | 0032258 A1 | 6/2000 |
| WO | 0172354 A2 | 10/2001 |
| WO | 2002015954 A1 | 2/2002 |
| WO | 0243866 A2 | 6/2002 |
| WO | 02082990 A1 | 10/2002 |
| WO | 03016882 A1 | 2/2003 |
| WO | 03039362 A1 | 5/2003 |
| WO | 03045233 A1 | 6/2003 |
| WO | 2004043250 A1 | 5/2004 |
| WO | 04092715 A1 | 10/2004 |
| WO | 2005051170 A2 | 6/2005 |
| WO | 2005082436 A1 | 9/2005 |
| WO | 05110601 A1 | 11/2005 |
| WO | 2005113036 A1 | 12/2005 |
| WO | 2006053007 A2 | 5/2006 |
| WO | 2007064835 A2 | 6/2007 |
| WO | 2007078937 A1 | 7/2007 |
| WO | 2008024810 A2 | 2/2008 |
| WO | 2008029403 A1 | 3/2008 |
| WO | 2008133702 A1 | 11/2008 |
| WO | 2009045462 A1 | 4/2009 |
| WO | 2009049252 A1 | 4/2009 |
| WO | 2009066287 A3 | 5/2009 |
| WO | 2009066288 A1 | 5/2009 |
| WO | 2009098648 A2 | 8/2009 |
| WO | 2009134380 A2 | 11/2009 |
| WO | 2010053702 A1 | 5/2010 |
| WO | 2010132077 A1 | 11/2010 |
| WO | 2010138848 A1 | 12/2010 |
| WO | 2010147659 A2 | 12/2010 |
| WO | 2011095483 A1 | 8/2011 |
| WO | 2012045667 A2 | 4/2012 |
| WO | 2012108959 A1 | 8/2012 |
| WO | 2012134588 A1 | 10/2012 |
| WO | 2012177353 A1 | 12/2012 |
| WO | 2012178134 A2 | 12/2012 |
| WO | 2013078200 A1 | 5/2013 |
| WO | 2013134486 A2 | 9/2013 |
| WO | 20130149186 A1 | 10/2013 |
| WO | 2013177565 A1 | 11/2013 |
| WO | 2013182321 A1 | 12/2013 |
| WO | 2014109898 A1 | 7/2014 |
| WO | 2014110538 A1 | 7/2014 |
| WO | 2014194183 A2 | 12/2014 |
| WO | 2015056259 A1 | 4/2015 |
| WO | 2015061493 A1 | 4/2015 |
| WO | 2015073211 A1 | 5/2015 |
| WO | 2015081337 A2 | 6/2015 |
| WO | 2015187366 A1 | 12/2015 |
| WO | 2016004088 A1 | 1/2016 |
| WO | 2016022650 A1 | 2/2016 |
| WO | 2016041873 A1 | 3/2016 |
| WO | 2016089702 A1 | 6/2016 |
| WO | 2016141082 A1 | 9/2016 |
| WO | 2016161254 A1 | 10/2016 |
| WO | 2017004278 A1 | 1/2017 |
| WO | 2017091624 A1 | 6/2017 |
| WO | 2017105600 A1 | 6/2017 |
| WO | 2017184988 A1 | 10/2017 |
| WO | 2017205816 A1 | 11/2017 |
| WO | 2018009614 A1 | 1/2018 |
| WO | 2018067748 A1 | 4/2018 |
| WO | 2018120104 A1 | 7/2018 |
| WO | 2018136799 A1 | 7/2018 |
| WO | 2018204568 A1 | 11/2018 |
| WO | 2019077482 A1 | 4/2019 |
| WO | 2019094440 A1 | 5/2019 |
| WO | 2019213493 A1 | 11/2019 |
| WO | 2019246381 A1 | 12/2019 |
| WO | 2020081393 A1 | 4/2020 |
| WO | 2021011738 A1 | 1/2021 |

OTHER PUBLICATIONS

Miontaser Eslam et al., "Seasonal Local Models for Glucose Prediction in Type 1 Diabetes", IEE Journal of Biomedical and Health Informatics, IEEE, Piscataway, NJ, USA, vol. 24, No. 7, Jul. 2020, pp. 2064-2072.

Samadi Sediqeh et al., "Automatic Detection and Estimation of Unannouced Meals for Multivariable Artificial Pancreas System", Diabetis Technology & Therapeutics, vol. 20m No. 3, Mar. 1, 2018, pp. 235-246.

Samadi Sediqeh et al., "Meal Detection and Carbohydrate Estimation Using Continuous Glucose Sensor Data" IEEE Journal of Biomedical and Health Informatics, IEEE, Piscataway, NJ, USA, vol. 21, No. 3, May 1, 2017, pp. 619-627.

Khodaei et al., "Physiological Closed-Loop Contol (PCLC) Systems: Review of a Modern Frontier in Automation", IEEE Access, IEEE, USA, vol. 8, Jan. 20, 2020, pp. 23965-24005.

E. Atlas et al., "MD-Logic Artificial Pancreas System: A pilot study in adults with type 1 diabetes", Diabetes Care, vol. 33, No. 5, Feb. 11, 2010, pp. 1071-1076.

Anonymous: "Fuzzy control system", Wikipedia, Jan. 10, 2020. URL: https://en.wikipedia.org/w/index.php?title=Fuzzy_control_system&oldid=935091190 Retrieved: May 25, 2021.

International Search Report and Written Opinion for the International Patent Application No. PCT/US2021/016283, dated Jun. 2, 2021, 15 pages.

International Search Report and Written Opinion for the International Patent Application No. PCT/US2021/022694, dated Jun. 25, 2021, 13 pages.

European Search Report for the European Patent Application No. 21168591.2, dated Oct. 13, 2021, 4 pages.

International Search Report and Written Opinion for the International Patent Application No. PCT/US2021/041954, dated Oct. 25, 2021, 13 pages.

International Search Report and Written Opinion for the International Patent Application No. PCT/US2021/047771, dated Dec. 22, 2021, 11 pages.

International Search Report and Written Opinion for the International Patent Application No. PCT/US2021/052855, dated Dec. 22, 2021, 11 pages.

International Search Report and Written Opinion for International Patent Application No. PCT/US2021/051027, dated Jan. 7, 2022, 16 pages.

International Search Report and Written Opinion for International Patent Application No. PCT/US2021/052372, dated Jan. 26, 2022, 15 pages.

International Search Report and Written Opinion for the International Patent Application No. PCT/US2021/046607, dated Jan. 31, 2022, 20 pages.

International Search Report and Written Opinion for the International Patent Application No. PCT/US2021/055745, dated Feb. 14, 2022, 13 pages.

(56) References Cited

OTHER PUBLICATIONS

Anonymous: "Artificial pancreas—Wikipedia", Mar. 13, 2018 (Mar. 13, 2018), XP055603712, Retrieved from the Internet URL: https://en.wikipedia.org/wiki/Artificial_pancreas [retrieved on Jul. 9, 2019] section "Medical Equipment" and the figure labeled "The medical equipment approach to an artifical pancreas".
Kaveh et al., "Blood Glucose Regulation via Double Loop Higher Order Sliding Mode Control and Multiple Sampling Rate." Paper presented at the proceedings of the 17th IFAC World Congress, Seoul, Korea (Jul. 2008).
Dassau et al., "Real-Time Hypoglycemia Prediction Suite Using Contineous Glucose Monitoring," Diabetes Care, vol. 33, No. 6, 1249-1254 (2010).
International Search Report and Written Opinion for International Patent Application No. PCT/US17/53262, dated Dec. 13, 2017, 8 pages.
Van Heusden et al., "Control-Relevant Models for Glucose Control using A Priori Patient Characteristics", IEEE Transactions on Biomedical Engineering, vol. 59, No. 7, (Jul. 1, 2012) pp. 1839-1849.
Doyle III et al., "Run-to-Run Control Strategy for Diabetes Management." Paper presented at 23rd Annual International Conference of the IEEE Engineering in Medicine and Biology Society, Istanbul, Turkey (Oct. 2001).
Bequette, B.W., and Desemone, J., "Intelligent Dosing Systems": Need for Design and Analysis Based on Control Theory, Diabetes Technology and Therapeutics 9(6): 868-873 (2004).
Parker et al., "A Model-Based Aogrithm for Blood Gucose Control in Type 1 Diabetic Patients." IEEE Transactions on Biomedical Engineering, 46 (2) 148-147 (1999).
International Search Report and Written Opinion for International Patent Application No. PCT/US2017/015601, dated May 16, 2017, 12 pages.
International Search Report and Written Opinion for the International Patent Application No. PCT/US2018/018901, dated Aug. 6, 2018, 12 pages.
International Search Report and Written Opinion for International Patent Application No. PCT/US2018/052467, dated Jan. 4, 2019, 13 pages.
"How to Create a QR Code that Deep Links to Your Mobile App", Pure Oxygen Labs, web<https://pureoxygenlabs.com/how-to-create-a-qr-codes-that-deep-link-to-your-mobile-app/> Year:2017.
"Read NFC Tags with an iPHone App on iOS 11", GoToTags, Sep. 11, 2017, web <https://gototags.com/blog/read-nfc-tags-with-an-iphone-app-on-ios-11/> (Year:2017).
International Search Report and Written Opinion for International Patent Application No. PCT/US2016/063350, dated Mar. 27, 2017, 9 pages.
Extended Search Report dated Aug. 13, 2018, issued in European Patent Application No. 16753053.4, 9 pages.
International Search Report and Written Opinion for International Patent Application No. PCT/US16/18452, dated Apr. 29, 2015, 9 pages.
International Preliminary Report on Patentability dated Aug. 31, 2017, issued in PCT Patent Application No. PCT/US2016/018452, 7 pages.
International Search Report and Written Opinion for International Patent Application No. PCT/US2019/055862, dated Mar. 11, 2020.
Unger, Jeff, et al., "Glucose Control in the Hospitalized Patient," Emerg. Med 36(9):12-18 (2004).
Glucommander FAQ downloaded from https://adaendo.com/GlucommanderFAQ.html on Mar. 16, 2009.
Finfer, Simon & Heritier, Stephane. (2009). The NICE-SUGAR (Normoglycaemia in Intensive Care Evaluation and Survival Using Glucose Algorithm Regulation) Study: statistical analysis plan. Critical care and resuscitation : journal of the Australasian Academy of Critical Care Medicine. 11. 46-57.
Letters to the Editor regarding "Glucose Control in Critically Ill Patients," N Engl J Med 361: 1, Jul. 2, 2009.
"Medtronic is Leading a Highly Attractive Growth Market," Jun. 2, 2009.
Davidson, Paul C., et al. "Glucommander: An Adaptive, Computer-Directed System for IV Insulin Shown to be Safe, Simple, and Effective in 120,618 Hours of Operation," Atlanta Diabetes Associates presentation Nov. 16, 2003.
Davidson, Paul C., et al. "Pumpmaster and Glucommander," presented at the MiniMed Symposium, Atlanta GA, Dec. 13, 2003.
Kanji S., et al. "Reliability of point-of-care testing for glucose measurement in critically ill adults," Critical Care Med, vol. 33, No. 12, pp. 2778-2785, 2005.
Krinsley James S., "Severe hypoglycemia in critically ill patients: Risk factors and outcomes," Critical Care Med, vol. 35, No. 10, pp. 1-6, 2007.
International Searching Authority, Invitation to Pay Additional Fees, International Application No. PCT/US2006/004929, dated Jul. 27, 2006.
Farkas et al. ""Single-Versus Triple-Lumen Central Catheter-Related Sepsis: A Prospective Randomized Study in a Critically Ill Population"" The American Journal of Medicine September 1992vol. 93 p. 277-282.
Davidson, Paul C., et al., A computer-directed intravenous insulin system shown to be safe, simple,and effective in 120,618 h of operation, Diabetes Care, vol. 28, No. 10, Oct. 2005, pp. 2418-2423.
Gorke, A. "Microbial contamination of haemodialysis catheter connections." EDTNA/ERCA journal (English ed.) vol. 31,2 (2005): 79-84. doi:10.1111/j.1755-6686.2005.tb00399.x.
Lovich et al. "Central venous catheter infusions: A laboratory model shows large differences in drug delivery dynamics related to catheter dead volume" Critical Care Med 2007 vol. 35, No. 12.
Van Den Berghe, Greet, M.D., Ph.D., et al., Intensive Insulin Therapy in Critically Ill Patients, The New England Journal of Medicine, vol. 345, No. 19, Nov. 8, 2001, pp. 1359-1367.
Templeton et al., "Multilumen Central Venous Catheters Increase Risk for Catheter-Related Bloodstream Infection Prospective Surveillance Study" Infection 2008; 36: 322-327.
Wilson, George S., et al., Progress toward the Development of an Implantable Sensor for Glucose, Clin. Chem., vol. 38, No. 9, 1992, pp. 1613-1617.
Yeung et al. "Infection Rate for Single Lumen v Triple Lumen Subclavian Catheters" Infection Control and Hospital Epidemiology, vol. 9, No. 4 (Apr. 1988) pp. 154-158 The University of Chicago Press.
International Search Report and Written Opinion, International Application No. PCT/US2010/033794 dated Jul. 16, 2010.
International Search Report and Written Opinion in PCT/US2008/079641 dated Feb. 25, 2009.
Berger, ""Measurement of Analytes in Human Serum and Whole Blood Samples by Near-Infrared Raman Spectroscopy,"" Ph D. Thesis, Massachusetts Institute of Technology, Chapter 4, pp. 50-73,1998.
Berger, "An Enhanced Algorithm for Linear Multivariate Calibration," Analytical Chemistry, vol. 70, No. 3, pp. 623-627, Feb. 1, 1998.
Billman et. al.,"Clinical Performance of an In line Ex-Vivo Point of Care Monitor: A Multicenter Study," Clinical Chemistry 48: 11, pp. 2030-2043, 2002.
Widness et al., "Clinical Performance on an In-Line Point-of-Care Monitor in Neonates"; Pediatrics, vol. 106, No. 3, pp. 497-504, Sep. 2000.
Finkielman et al., "Agreement Between Bedside Blood and Plasma Glucose Measurement in the ICU Setting"; retrieved from http://www.chestjournal.org; CHEST/127/5/May 2005.
Glucon Critical Care Blood Glucose Monitor; Glucon; retrieved from http://www.glucon.com.
Fogt, et al., "Development and Evaluation of a Glucose Analyzer for a Glucose-Controlled Insulin Infusion System (Biostator)"; Clinical Chemistry, vol. 24, No. 8, pp. 1366-1372, 1978.
Vonach et al., "Application of Mid-Infrared Transmission Spectrometry to the Direct Determination of Glucose in Whole Blood," Applied Spectroscopy, vol. 52, No. 6, 1998, pp. 820-822.
Muniyappa et al., "Current Approaches for assessing insulin sensitivity and resistance in vivo: advantages, limitations, and appropriate usage," AJP-Endocrinol Metab, vol. 294, E15-E26, first published Oct. 23, 2007.

(56) References Cited

OTHER PUBLICATIONS

R Anthony Shaw, et al., "Infrared Spectroscopy in Clinical and Dianostic Analysis," Encyclopedia of Analytical Chemistry, ed. Robert A. Meyers, John Wiley & Sons, Ltd., pp. 1-20, 2000.
International Preliminary Report on Patentability for the International Patent Application No. PCT/US2019/053603, dated Apr. 8, 2021, 9 pages.
International Search Report and Written Opinion for the International Patent Application No. PCT/US2019/053603, dated Jan. 7, 2020, 16 pages.
Dassau et al., "Detection of a meal using continuous glucose monitoring: Implications for an artificial [beta]-cell." Diabetes Care, American Diabetes Association, Alexandria, VA, US, 31(2):295-300 (2008).
Cameron et al., "Probabilistic Evolving Meal Detection and Estimation of Meal Total Glucose Appearance Author Affiliations", J Diabetes Sci and Tech,Vol., Diabetes Technology Society ;(5):1022-1030 (2009).
Lee et al., "A closed-loop artificial pancreas based on model predictive control: Human-friendly identification and automatic meal disturbance rejection", Biomedical Signal Processing and Control, Elsevier, Amsterdam, NL, 4 (4): 1746-8094 (2009).
International Search Report and Written Opinion for the InternationalPatent Application No. PCT/US2021/018297, dated May 18, 2021, 18 pages.
An Emilia Fushimi: "Artificial Pancreas: Evaluating the ARG Algorithm Without Meal Announcement", Journal of Diabetes Science and Technology Diabetes Technology Society, Mar. 22, 2019, pp. 1025-1043.
International Search Report and Written Opinion for the International Patent Application No. PCT/US2021/017441, dated May 25, 2021, 12 pages.
International Search Report and Written Opinion for the InternationalPatent Application No. PCT/US2021/017664, dated May 26, 2021, 16 pages.
Mirko Messori et al: "Individualized model predictive control for the artificial pancreas: In silico evaluation of closed-loop glucose control", IEEE Control Systems, vol. 38, No. 1,Feb. 1, 2018, pp. 86-104.
International Search Report and Written Opinion for the International Patent Application No. PCT/US2021/017662, dated May 26, 2021, 14 pages.
Anonymous: "Reservoir Best Practice and Top Tips" Feb. 7, 2016, URL: https://www.medtronic-diabetes.co.uk/blog/reservoir-best-practice-and-top-tips, p. 1.
Gildon Bradford: "InPen Smart Insulin Pen System: Product Review and User Experience" Diabetes Spectrum, vol. 31, No. 4, Nov. 15, 2018, pp. 354-358.
International Search Report and Written Opinion for the International Patent Application No. PCT/US2021/016050, dated May 27, 2021, 16 pages.
International Search Report and Written Opinion for the International Patent Application No. PCT/US2020/065226, dated May 31, 2021, 18 pages.
International Search Report and Written Opinion for the International Patent Application No. PCT/US2021/017659, dated May 31, 2021, 13 pages.
International Search Report and Written Opinion for the International Patent Application No. PCT/US2020/052125, dated Aug. 12, 2020, 15 pages.
International Search Report and Written Opinion for the International Patent Application No. PCT/US2020/050332, dated Sep. 12, 2020, 12 pages.
European Patent Office, "Notification of Transmittal of the ISR and the Written Opinion of the International Searching Authority, or the Declaration," in PCT Application No. PCT/GB2015/050248, Jun. 23, 2015, 12 pages.
International Search Report and Written Opinion for the International Patent Application No. PCT/US2022/012896, dated Apr. 22, 2022, 15 pages.
International Search Report and Written Opinion for the International Patent Application No. PCT/US2022/013470, dated May 6, 2022, 14 pages.
International Search Report and Written Opinion for the International Patent Application No. PCT/US2022/013473, dated May 6, 2022, 13 pages.
International Search Report and Written Opinion for the International Patent Application No. PCT/US2022/019079, dated Jun. 2, 2022, 14 pages.
International Search Report and Written Opinion for the International Patent Application No. PCT/US2022/018453, dated Jun. 2, 2022, 13 pages.
International Search Report and Written Opinion for the International Patent Application No. PCT/US22/018700, dated Jun. 7, 2022, 13 pages.
International Search Report and Written Opinion for the International Patent Application No. PCT/US22/019080, dated Jun. 7, 2022, 14 pages.
International Search Report and Written Opinion for the International Patent Application No. PCT/US22/019664, dated Jun. 7, 2022, 14 pages.
International Search Report and Written Opinion for the International Patent Application No. PCT/US21/060618, dated Mar. 21, 2022, 15 pages.
Herrero Pau et al: "Enhancing automatic closed-loop glucose control in type 1 diabetes with an adaptive meal bolus calculator-in silicoevaluation under intra-day variability", Computer Methods and Programs in Biomedicine, Elsevier, Amsterdam, NL, vol. 146, Jun. 1, 2017 (Jun. 1, 2017), pp. 125-131, XP085115607, ISSN: 0169-2607, DOI:10.1016/J.CMPB.2017.05.010.
Marie Aude Qemerais: "Preliminary Evaluation of a New Semi-Closed-Loop Insulin Therapy System over the prandial period in Adult Patients with type I diabetes: the WP6. 0 Diabeloop Study", Journal of Diabetes Science and Technology Diabetes Technology Society Reprints and permissions, Jan. 1, 2014, p. 1177-1184, Retrieved from the Internet: URL:http://journals.sagepub.com/doi/pdf/10.1177/1932296814545668 [retrieved on Jun. 6, 2022] chapter "Functioning of the Algorithm" chapter "Statistical Analysis" p. 1183, left-hand column, line 16-line 23.
Anonymous: "Kernel density estimation", Wikipedia, Nov. 13, 2020 (Nov. 13, 2020), pp. 1-12, XP055895569, Retrieved from the Internet: URL:https://en.wikipedia.org/w/index.php?title=Kemnel_density_estimation&oldid=988508333 [retrieved on Jun. 6, 2022].
Anonymous: "openaps / orefO /lib/determine-basal-js", openaps repository, Nov. 9, 2019 (Nov. 9, 2019), pp. 1-17, XP055900283, Retrieved from the Internet: URL:https://github.com/openaps/oref0/blob/master/lib/determine-basal/determine-basal.js [retrieved on Jun. 6, 2022] line 116-line 118, line 439-line 446.
Anonymous: "AndroidAPS screens", AndroidAPS documentation, Oct. 4, 2020 (Oct. 4, 2020), pp. 1-12, XP055894824, Retrieved from the Internet: URL:https://github.com/openaps/AndroidAPSdocs/blob/25d8acf8b28262b411b34f416f173ac0814d7e14/docs/EN/Getting-Started/Screenshots.md [retrieved on Jun. 6, 2022].
Kozak Milos et al.: "Issue #2473 of AndroidAPS", MilosKozak / AndroidAPS Public repository, Mar. 4, 2020 (Mar. 4, 2020), pp. 1-4, XP055900328, Retrieved from the Internet: URL:https://github.com/MilosKozak/AndroidAPS/issues/2473 [retrieved on Jun. 6, 2022].
Medication Bar Code System Implementation Planning Section I: A Bar Code Primer for Leaders, Aug. 2013.
Medication Bar Code System Implementation Planning Section II: Building the Case for Automated Identification of Medications, Aug. 2013.
Villareal et al. (2009) in: Distr. Comp. Art. Intell. Bioninf. Soft Comp. Amb. Ass. Living; Int. Work Conf. Art. Neural Networks (IWANN) 2009, Lect. Notes Comp. Sci. vol. 5518; S. Omatu et al. (Eds ), pp. 870-877.
Fox, Ian G.; Machine Learning for Physiological Time Series: Representing and Controlling Blood Glucose for Diabetes Management; University of Michigan. ProQuest Dissertations Publishing, 2020. 28240142. (Year: 2020).

\* cited by examiner

800

```
┌─────────────────────────────────────────────────────────────┐
│ Determining, by a processor coupled to a medical device,    │
│ that the medical device has delivered more than a preset    │   810
│ volume of insulin over a set amount of time                 │
└─────────────────────────────────────────────────────────────┘
                              │
                              ▼
┌─────────────────────────────────────────────────────────────┐
│ Adjusting an amount of insulin to be delivered by the       │
│ medical device as an adjusted basal dosage based on a       │
│ calculation using a volume of insulin delivered over the    │   820
│ set amount of time and a total daily insulin to be          │
│ delivered as calculated by an artificial pancreas algorithm │
└─────────────────────────────────────────────────────────────┘
                              │
                              ▼
┌─────────────────────────────────────────────────────────────┐
│ Limiting the amount of insulin to be delivered as the       │
│ adjusted basal dosage to a maximum volume of a user's       │
│ basal insulin delivery volume divided by either a time      │   830
│ increment, less than an hour, at which the adjusted basal   │
│ dosage is administered or a percentage of an hourly         │
│ basal rate                                                  │
└─────────────────────────────────────────────────────────────┘
```

```
┌─────────────────────────────────────────────────────────────────────────────┐
│ Determine that a medical device has been delivering insulin below a fixed    │
│ personalized basal rate for a period of time of insulin delivery history     │
└─────────────────────────────────────────────────────────────────────────────┘
                                     │
                                     ▼  915

┌─────────────────────────────────────────────────────────────────────────────┐
│ Determine that the negative insulin on board value is greater than a         │
│ multiple of a user's total daily insulin-based hourly basal value            │
└─────────────────────────────────────────────────────────────────────────────┘
                                     │
                                     ▼  925

┌─────────────────────────────────────────────────────────────────────────────┐
│ In response to the negative insulin on board value being greater than a      │
│ multiple of the user's total daily insulin-based hourly basal value, alter   │
│ delivery of insulin by the medical device to deliver a total daily-based     │
│ basal or a personalized volume of insulin                                    │
└─────────────────────────────────────────────────────────────────────────────┘
                                     │
                                     ▼  935

┌─────────────────────────────────────────────────────────────────────────────┐
│ output a notification message requesting a user to acknowledge the altered   │
│ delivery of insulin or request a new calibration value in calculating a      │
│ calibrated amount of insulin for delivery                                    │
└─────────────────────────────────────────────────────────────────────────────┘
                                     │  945
                                     ▼  955
                         ◇ Receive a user acknowledgement or ◇
                         ◇ request for the new calibration value? ◇
                 User Acknowledgement                Request Recieved
                     Received                                │  965
                         │ 962                               ▼
                         ▼                      ┌──────────────────────────┐
              ┌────────────────────┐            │ Generate the new         │
              │ Continue the       │            │ calibration value in an  │
              │ altered delivery   │   975      │ artificial pancreas      │
              │ of insulin         │            │ algorithm executed by    │
              └────────────────────┘            │ the processor            │
                                                └──────────────────────────┘
                                                             │
                                                             ▼
                                                ┌──────────────────────────┐
                                                │ Apply the new            │
                                                │ calibration value in the │
                                                │ artificial pancreas      │
                                                │ algorithm executed by    │
                                                │ the processor to         │
                                                │ calculate the calibrated │
                                                │ amount of insulin for    │
                                                │ delivery                 │
                                                └──────────────────────────┘
```

```
┌─────────────────────────────────────────────────────────┐
│ Determining, by a processor coupled to a glucose sensor,│
│ insulin delivery is not attenuating at a rate suitable  │         1110
│ to recover from a hypoglycemic event                    │
└─────────────────────────────────────────────────────────┘
                            │
                            ▼
┌─────────────────────────────────────────────────────────┐
│ In response to the determination, increasing a likelihood│
│ of suspension of insulin by either:                     │
│ reducing a penalty of estimated outcomes within an      │
│ artificial pancreas algorithm such that a requested     │         1120
│ insulin delivery is below a user-inputted basal delivery,│
│ or scaling deviations of insulin delivery that are below│
│ the user-inputted basal delivery to be proportional to  │
│ the user-inputted basal delivery                        │
└─────────────────────────────────────────────────────────┘
```

```
┌─────────────────────────────────────────────────────────┐
│ Determining, by a processor coupled to a glucose sensor,│
│ during exercise or other activity that may induce       │
│ increased hypoglycemic risk that insulin delivery is    │    1210
│ not attenuating at rate suitable to maintain            │
│ glucose concentrations                                  │
└─────────────────────────────────────────────────────────┘
                              │
                              ▼
┌─────────────────────────────────────────────────────────┐
│ In response to the determination, altering either a     │
│ control target glucose value by increasing the control  │
│ target glucose value to a glucose value higher than     │    1220
│ the current target glucose value, or an input basal     │
│ delivery by reducing the input basal delivery to an     │
│ input basal value lower than a current input basal value│
└─────────────────────────────────────────────────────────┘
                              │
                              ▼
┌─────────────────────────────────────────────────────────┐
│ Attenuating insulin delivery at a more rapid rate to    │    1230
│ maintain glucose concentrations.                        │
└─────────────────────────────────────────────────────────┘
```

FIG. 12

SAFETY CONSTRAINTS FOR A CONTROL ALGORITHM BASED DRUG DELIVERY SYSTEM

CROSS-REFERENCE TO RELATED APPLICATION

This application claims priority to U.S. Provisional Patent Application No. 62/667,118, filed on May 4, 2018, the entire contents of which are hereby incorporated by reference.

TECHNICAL FIELD

The described examples provide safety constraints for a drug delivery system that provides automatic delivery of a drug based on sensor input to ensure that users do not over or under deliver medication provided automatically based on the control algorithm.

BACKGROUND

Medication delivery systems typically delivery a medication to a user based on health conditions of the user. For example, a control algorithm-based drug delivery systems can monitor a user's glucose levels, determine an appropriate level of medication, such as insulin, for the user based on the monitored medical conditions, such as glucose levels, and subsequently dispense the medication to the user. The control algorithms used in control algorithm-based drug delivery systems and other medication delivery systems generally rely on data provided by users and/or expected glucose and medication levels determined by different means, such as insulin deliveries and the provided user data. However, the provided data or expected levels may be incorrect or erroneous, which may lead to incorrect medication dosages and incorrect medication delivery schedules. Data and measurement errors may result due to many different reasons, such as user confusion (e.g., have incorrect time, input incorrect numbers, or the like), glucose sensor drift or bias (which may be due to many different factors related to the glucose sensor), errors in the medication delivery system, or the like. As a result, conventional medication delivery systems do not provide safety constraints that enable automated medication delivery systems to respond to incorrect data and measurement errors. A need therefore exists for a medication delivery system, such as an insulin management system, that includes such features as safety constraints, alerts and remedial actions.

SUMMARY

Disclosed is a non-transitory computer readable medium embodied with programming code executable by a processor. The processor when executing the programming code is operable to perform functions, including functions to receive at regular time intervals a value of a glucose measurement via a wireless connection with a glucose monitor. The glucose measurement is performed by the glucose monitor. Future glucose values may be predicted based on prior glucose measurement values. An insulin basal delivery rate may be adjusted to be provided by a medical device based on the predicted future glucose values. Insulin may be delivered via the medical device according to the adjusted insulin basal delivery rate.

Disclosed is a method performed by a processor coupled to a glucose monitor via a wireless connection. The method includes receiving, by the processor from the glucose monitor, a number of glucose measurement values. Each glucose measurement value of the number of glucose measurement values is received at a regular time interval over a period of time and the regular time interval is less than the period of time. A number of future glucose measurement values may be predicted using at least one of the number of received glucose measurement values. It may be determined that a subsequent glucose measurement value has not been received within a next regular time interval. In response to the determination that the subsequent glucose measurement value has not arrived, a total daily insulin-based basal delivery rate may be adjusted to be provided by a medical device based on at least one of the predicted number of future glucose measurement values. Insulin may be delivered via the medical device according to the adjusted total daily insulin-based basal delivery rate.

Disclosed is another method in which a processor coupled to a medical device determines that the medical device has delivered more than a preset volume of insulin over a set amount of time. The preset volume of insulin is based on one or more of: a user input basal rate, a rate calculated by an artificial pancreas algorithm using an average daily delivery rate, a rate based on user weight and/or user age, a total daily insulin delivered, or a total daily basal delivered. In response to the determination, an amount of insulin to be delivered by the medical device as an adjusted basal dosage is adjusted based on a calculation using a volume of insulin delivered over the set amount of time and a total daily insulin to be delivered as calculated by an artificial pancreas algorithm.

Disclosed is a system that includes a medical device, a sensor and a management device. The medical device includes a pump, a reservoir configured to contain insulin, a processor and a transceiver, and the medical device is operable to deliver insulin in response to outputs from the processor. The sensor may include a transmitter, a processor and a cannula. The sensor is operable to measure blood glucose and output a blood glucose value. The management device may include a processor, a memory configured to store an artificial pancreas algorithm and a transceiver. The artificial pancreas algorithm is operable to determine times and dosages of insulin to be delivered to a user, the times and dosages may be calculated based on a user's sex, a user's age, a user's weight, a user's height, and/or on glucose levels provided by the sensor. The processor of the management device upon execution of the artificial pancreas algorithm is operable to determine an occurrence of a hypoglycemic event. In response to the determination of the occurrence of the hypoglycemic event, a glucose rate of change filter may be implemented for a predetermined period of time. The rate of change filter limits a rate of change in measured blood glucose values used by the artificial pancreas algorithm in the determination of a time for delivery of insulin and a dosage of the insulin being delivered. The processor instructs the medical device deliver the determined dosage of the insulin at the determined time for delivery.

Disclosed is yet another method including determining, by a processor of a medical management device in response to receipt of a glucose measurement value from a sensor, that a medical device has been delivering insulin below a fixed personalized basal rate for a period of time of insulin delivery history. A result of delivering insulin below a fixed personalized basal rate is a negative insulin on board value. The processor may determine that the negative insulin on board value is greater than three times a user's total daily insulin-based hourly basal value. In response to the negative insulin on board value being greater than a multiple of a user's total daily insulin-based hourly basal value, delivery of insulin by the medical device may be altered to deliver a total daily-based basal or a personalized volume of insulin. A notification message may be output requesting the user to acknowledge the altered delivery of insulin or a requirement for a new calibration value for use by the processor in calculating a calibrated amount of insulin for delivery.

Disclosed is another example of a non-transitory computer readable medium embodied with programming code executable by a processor. The processor when executing the programming code is operable to perform functions, including functions to obtain a series of glucose concentration values as measured at regular time intervals by a glucose monitor. The processor may detect a rapid rate of increase in a glucose concentration. In reaction to the detection of the rapid rate of increase in the glucose concentration, the processor may implement a response to the rapid rate of increase in the glucose concentration.

An example of another method is disclosed in which a processor coupled to a glucose sensor determines insulin delivery is not attenuating at a rate suitable to recover from a hypoglycemic event. In response to the determination, a likelihood of suspension of insulin may be increasing by either: reducing a penalty of estimated outcomes within an artificial pancreas algorithm such that a requested insulin delivery is below a user-inputted basal delivery or scaling deviations of insulin delivery that are below the user-inputted basal delivery to be proportional to the user-inputted basal delivery.

A further example of a method is disclosed in which a processor coupled to a glucose sensor determines during exercise or other activity that may induce increased hypoglycemic risk that insulin delivery is not attenuating at rate suitable to maintain glucose concentrations. In response to the determination, either the control target glucose value may be increasing to a glucose value higher than the current target glucose value or the input basal delivery may be reduced to an input basal value lower than a current input basal value.

BRIEF DESCRIPTION OF THE DRAWINGS

FIG. 8 shows a flow chart of a process example for implementing an example of a safety constraint in response to an over-delivery of insulin.

FIG. 9 shows a flow chart of a process example for implementing an example of a safety constraint in response to an under-delivery of insulin.

FIG. 11 shows a flow chart of a process example for implementing an example of a response that increases a likelihood of suspension of insulin.

FIG. 12 shows a flow chart of a process example for implementing an example of a response that attenuates insulin delivery.

DETAILED DESCRIPTION

Various examples provide safety constraints for a control algorithm-based drug delivery system, also referred to as an "artificial pancreas" algorithm-based system or more generally an artificial pancreas algorithm, that provides automatic delivery of a drug based on sensor input. For example, the artificial pancreas (AP) algorithm when executed by a processor enables a system to monitor a user's glucose levels, determine an appropriate level of insulin for the user based on the monitored glucose levels (e.g., glucose concentrations or glucose measurement values) and other information, such as user-provided information, and subsequently dispense insulin to the user. In addition, the AP algorithm utilizes the monitored glucose levels and other information to generate and send a command to a medical device, such as a pump, to control, for example, deliver a bolus dose of insulin to the user, change the amount or timing of future doses, or other controllable functions. The safety constraints described herein provide safe operation of the drug delivery system during various operational scenarios including, for example, during times when the sensor input is missing or erroneous, unexpected events such as an unplanned meal. The disclosed safety constraints mitigate under-delivery or over-delivery of the drug while not overly burdening the user of the drug delivery system and without sacrificing performance of the drug delivery system.

Figure 1:
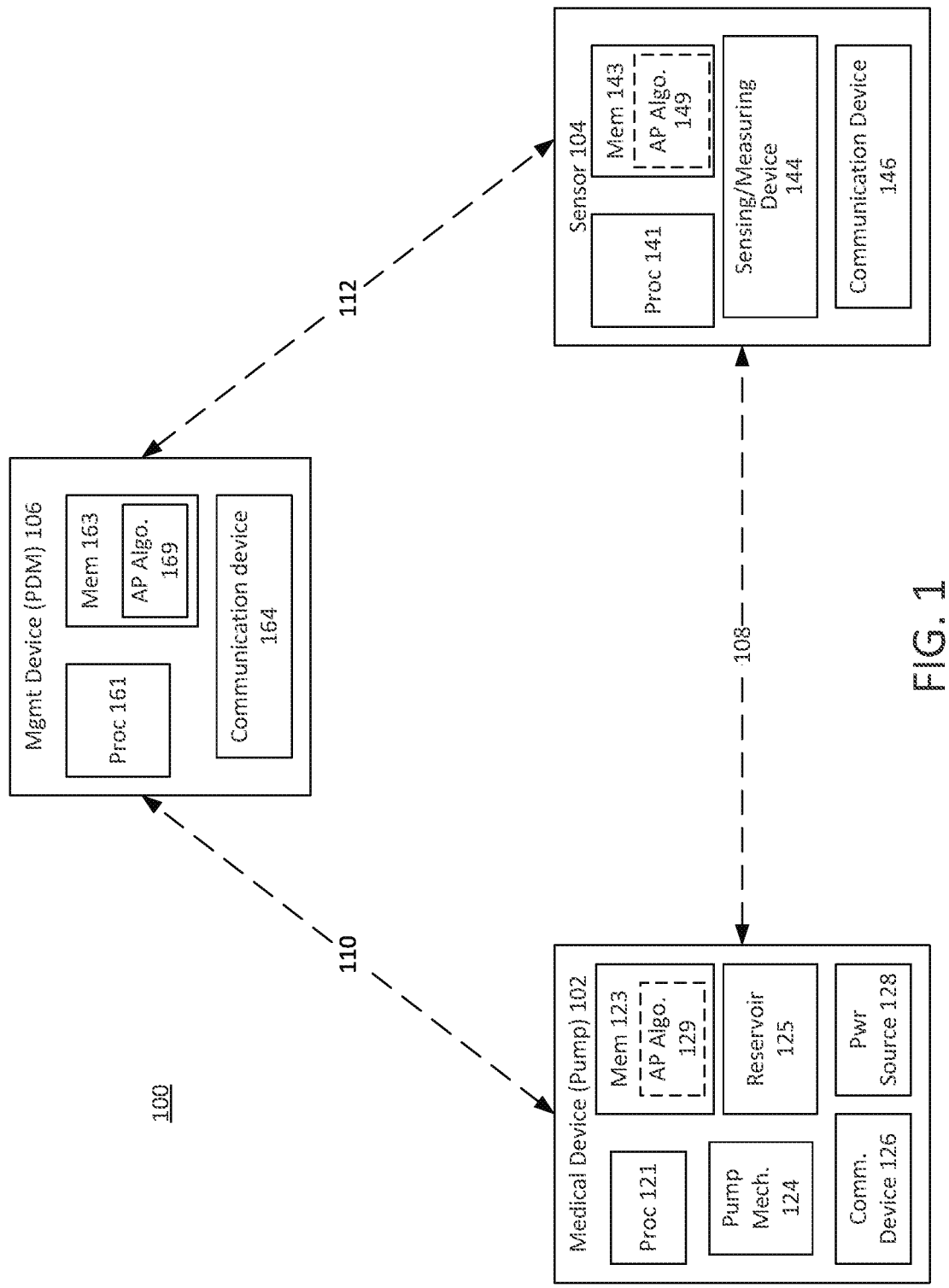
FIG. 1 illustrates an example of a drug delivery system operable to implement the techniques and processes described herein.

FIG. 1 illustrates an example of a drug delivery system 100. The drug delivery system 100 can include a medical device 102, a sensor 104, and a management device (PDM) 106. In various examples, the drug delivery system 100 can be an automated drug delivery system. In various examples, the medical device 102 can be attached to the body of a user or patient and can deliver any therapeutic agent, including any drug or medicine, such as insulin or the like, to a user. For example, the medical device 102 can be a wearable device. For example, the medical device 102 can be directly coupled to a user (e.g., directly attached to a body part and/or skin of the user). For example, a surface of the medical device 102 can include an adhesive to facilitate attachment to a user.

The medical device 102 can include a number of components to facilitate automated delivery of a drug (also referred to as a therapeutic agent) to the user. The medical device 102 can store and provide any medication or drug to the user. In various examples, the medical device 102 can be an automated, wearable insulin delivery device. For example, the medical device 102 can include a reservoir 125 for storing the drug (such as insulin), a needle or cannula for delivering the drug into the body of the user, and a pump mechanism (mech.) 124 or other drive mechanism for transferring the drug from the reservoir 125, through the needle or cannula (not shown), into the body of the user. The medical device 102 can also include a power source 128 such as a battery for supplying power to the pump mechanism 124 and/or other components (such as the processor 121, memory 123, and the communication device 126) of the medical device 102. The medical device 102 is often referred to as a pump, or an insulin pump, in reference to the operation of expelling a drug from the reservoir 125 for delivery to the user. The reservoir 125 may be configured to store insulin, morphine, or another drug suitable for automated delivery.

The medical device 102 can provide the stored therapeutic agent to the user based on information provided by the sensor 104 and/or the management device (PDM) 106. For example, the medical device 102 can also contain analog and/or digital circuitry that may be implemented as a processor 121 (or controller) for controlling the delivery of the medication. The circuitry may be used to implement the processor 121, and may include discrete, specialized logic and/or components, an application-specific integrated circuit, a microcontroller or processor that executes software instructions, firmware, programming instructions (such as artificial pancreas algorithm 129) stored in memory devices (such as memory 123), or any combination thereof. In various examples, the processor 161 can be configured to cause the pump to deliver doses of the medication to a user at predetermined intervals. For example, the processor 161 may execute a control algorithm, such as an artificial pancreas algorithm (AP Algo) 169. The size and/or timing of the doses may be programmed, for example, into an artificial pancreas algorithm 169 using a wired or wireless link by the user or by a third party (such as a health care provider, medical device manufacturer, or the like).

Instructions for determining the delivery of the medication to the user (e.g., the size and/or timing of any doses of the medication) can originate locally (e.g., based on programming instructions, such as an instance of the artificial pancreas algorithm 129, stored in the memory 123 that is coupled to the medical device 102 used to make determinations by the medical device 102) or can originate remotely and be provided to the medical device 102. Remote instructions can be provided to the medical device 102 over a wired or wireless link by the electronic device (PDM) 106, which executes the artificial pancreas algorithm 169. The medical device 102 can execute any received instructions (originating internally or from the management device 106 for the delivery of the medication to the user. In this way, under either scenario, the delivery of the medication to a user can be automated.

In various examples, the medical device 102 can communicate via a wireless link 110 with the management device 106. The management device 106 can be any electronic device such as, for example, an Apple Watch®. The management device 106 can be a wearable wireless accessory device. The wireless links 108, 110 and 112 may be any type of wireless link provided by any known wireless standard. As an example, the wireless links 108, 110 and 112 may enable communications between the medical device 102, the management device 106 and sensor 104 based on Bluetooth®, Wi-Fi®, a near-field communication standard, a cellular standard, or any other wireless optical or radio-frequency protocol.

The sensor 104 may be a glucose sensor operable to measure blood glucose and output a blood glucose value or data that is representative of a blood glucose value. For example, the sensor 104 may be a glucose monitor or a continuous glucose monitor (CGM). The sensor 104 may include a processor 141, a memory 143, a sensing/measuring device 144, and communication device 146. The communication device 146 of sensor 104 can include one or more sensing elements, an electronic transmitter, receiver, and/or transceiver for communicating with the management device 106 over a wireless link 112 or with medical device 102 over the link 108. The sensing/measuring device 144 may include one or more sensing elements, such as a glucose measurement, heart rate monitor, or the like. For example, the sensor 104 can be a continuous glucose monitor (CGM). The processor 141 may include discrete, specialized logic and/or components, an application-specific integrated circuit, a microcontroller or processor that executes software instructions, firmware, programming instructions stored in memory devices (such as memory 143), or any combination thereof. For example, the memory 143 may store an instance of an AP algorithm 149 that is executable by the processor 141. Although the sensor 104 is depicted as separate from the medical device 102, in various examples, the sensor 104 and medical device 102 may be incorporated into the same unit. That is, in various examples, the sensor 104 can be a part of the medical device 102 and contained within the same housing of the medical device 102 (e.g., the sensor 104 can be positioned within or embedded within the medical device 102). Glucose monitoring data (e.g., measured glucose values) determined by the sensor 104 can be provided to the medical device 102 and/or the management device 106 and can be used to adjust automated delivery of insulin by the medical device 102. The management device 106 can be a personal diabetes manager.

The sensor 104 can also be coupled to the user by, for example, adhesive or the like and can provide information or data on one or more medical conditions and/or physical attributes of the user. The information or data provided by the sensor 104 may be used to adjust drug delivery operations of the medical device 102. The management device 106 can be used to program or adjust operation of the medical device 102 and/or the sensor 104. The management device 106 can be any portable electronic device including, for example, a dedicated controller, such as processor 161, a smartphone, or a tablet. In an example, the management device (PDM) 106 may include a processor 161, a management device memory 163, and a communication device 164. The management device 106 may contain analog and/or digital circuitry that may be implemented as a processor 161 (or controller) for executing processes to manage a user's glucose and for controlling the delivery of the medication. The processor 161 may also be operable to execute programming code stored in the management device memory 163. For example, the management device memory 163 may be configured to store an artificial pancreas algorithm 169 that may be executed by the processor 161. The processor 161 may when executing the artificial pancreas algorithm 169 may be operable to perform various functions, such as those described with respect to the examples in the figures. The communication device 164 may be a receiver, a transmitter or a transceiver that operates according to one or more radio-frequency protocols.

The medical device 102 and the sensor 104 may communicate over a wireless link 108. The medical device 102 and the management device 106 may communicate over a wireless link 110. The sensor 104 and the management device 106 may communicate over a wireless link 112. The wireless links 108, 110, and 112 may be any type of wireless link provided by any known wireless standard. As an example, the wireless links 108, 110, and 112 can provide communication links based on Bluetooth, Wi-Fi, a near-field communication standard, a cellular standard, or any other wireless protocol via the respective communication devices 126, 146 and 164. In some examples, the medical device 102 and/or the management device 106 may include a user interface, such a keypad, a touchscreen display, buttons, a microphone, a speaker, a display or the like, that is operable to allow a user to enter information and allow the management device to output information for presentation to the user.

In various examples, the drug delivery system 100 can be an insulin drug delivery system. In various examples, the medical device 102 can be the OmniPod® (Insulet Corporation, Billerica, Mass.) insulin delivery device as described in U.S. Pat. Nos. 7,303,549, 7,137,964, or U.S. Pat. No. 6,740,059, each of which is incorporated herein by reference in its entirety.

In various examples, the drug delivery system 100 can implement the artificial pancreas (AP) algorithm (and/or provide AP functionality) to govern or control automated delivery of insulin to a user (e.g., to maintain euglycemia—a normal level of glucose in the blood). The AP algorithm can be implemented by the medical device 102 and/or the sensor 104. The AP algorithm can be used to determine the times and dosages of insulin delivery. In various examples, the AP algorithm can determine the times and dosages for delivery based on information known about the user, such as the user's sex, age, weight, or height, and/or on information gathered about a physical attribute or condition of the user (e.g., from the sensor 104). For example, the AP algorithm may determine an appropriate delivery of insulin based on glucose level monitoring of the user through the sensor 104. The AP algorithm may also allow the user to adjust insulin delivery. For example, the AP algorithm may allow the user to issue (e.g., via an input) commands to the medical device 102, such as a command to deliver an insulin bolus. In some examples, different functions of the AP algorithm may be distributed among two or more of the management device 106, the pump 102 or the sensor 104. In other examples, the different functions of the AP algorithm may be performed by one device, such the management device 106, the pump 102 or the sensor 104. In various examples, the drug delivery system 100 can operate according to or can include any of the features or functionalities of the drug delivery systems described in U.S. patent application Ser. No. 15/359,187, filed Nov. 22, 2016, which is herein incorporated by reference in its entirety.

As described herein, the drug delivery system 100 or any component thereof can be considered to provide AP functionality or to implement an AP algorithm. Accordingly, references to the AP algorithm (e.g., functionality, operations, or capabilities thereof) are made for convenience and can refer to and/or include operations and/or functionalities of the drug delivery system 100 or any constituent component thereof (e.g., the medical device 102 and/or the management device 106). The drug delivery system 100—for example, as an insulin delivery system implementing an AP algorithm—can be considered to be a drug delivery system or an AP algorithm-based delivery system that uses sensor inputs (e.g., data collected by the sensor 104).

Since the drug delivery system 100 relies on sensor input for proper operation of drug delivery, the drug delivery system 100 may impose delivery limits for safety reasons. While delivery constraints may be imposed to ensure safe automatic delivery of a drug (e.g., insulin) to the user, it may be, in some examples, desirable to not have the constraints overly reduce AP algorithm control performance or to overly burden the user. Techniques described herein enable the drug delivery system 100 to maximize user safety while optimizing glucose control performance and minimizing any additional burden or inconvenience placed on the user.

The sensor 104—for example, as a CGM—can operate with or otherwise exhibit sensor bias, drift, or other discrepancies of determined data values that could lead to over-delivery or under-delivery of a drug to the user. The techniques described herein provide safety constraints for operation of the drug delivery system 100 that include safety mitigations in case of failure of the sensor 104, errant values provided by the sensor 104, and/or missing data from the sensor 104, as well as from other risks associated with relying on the sensor 104. The techniques described herein also provide safety constraints specific to higher risk conditions such as lower glucose values and a response of the implemented AP algorithm to outside perturbations, such as rescue carbohydrates or the like.

The drug delivery system 100, in some examples, may be a wearable, automated drug delivery system that includes the medical device 102, the sensor 104, and a management device 106. In one example of a wearable, automated drug delivery system, the medical device 102 may be a wearable insulin delivery device, the management device 106 may be a handheld electronic computing device, and the sensor 104 may be a continuous glucose monitor. The management device 106 can be a mobile device or cellphone or can be a dedicated custom electronic device. As part of a wearable, automated drug delivery system, the medical device 102 and the sensor 104 may each be directly coupled to a user.

The sensor 104 can provide sensor data to the medical device 102 and/or the management device 106. The management device 106 can include a controller or processor and a memory. The memory can store instructions that can be executed by the controller or processor. The instructions can implement an "artificial pancreas" algorithm when executed. In general, the management device 106 can include a controller for determining a delivery of insulin to the user (e.g., in terms of dosage amounts and times) based on data from the sensor 104 and providing a corresponding instruction regarding the determined delivery of the insulin to the medical device 102.

In various examples, as mentioned above, the sensor 104 can be provided as part of or embedded within the wearable insulin delivery device 102. Additionally, in various examples, as mentioned above, the system 100 can include an intermediate wireless device (e.g., the management device 106) that can relay information wirelessly between the devices depicted in FIG. 1.

In general, the system 100 can automatically monitor glucose levels of the user, automatically determine a delivery of insulin to the user based on the monitored glucose levels, and automatically provide the determined amount of insulin to the user. Each of these steps can be performed without any user input or interaction. In various examples, a user confirmation can be required before the insulin is provided to the user as discussed above. For example, when management device 106 is implemented as a cellphone, for added security, the user can be required to confirm or acknowledge the determined delivery of insulin to the user. Without receiving such confirmation, the insulin delivery may be blocked or prevented. This security feature can mitigate hacking or other cybersecurity risks.

In various examples, the drug delivery system 100 can operate such that glucose values are regularly provided by the sensor 104 to the AP algorithm executing on a processor (e.g., to the medical device 102 and/or the management device 106). For example, glucose values can be provided periodically such as, for example, approximately every 5 minutes (e.g., corresponding to a control cycle of the system 100) or the like. The medical device 102 can adjust an amount of insulin for delivery based on the received glucose values.

Figure 7A:
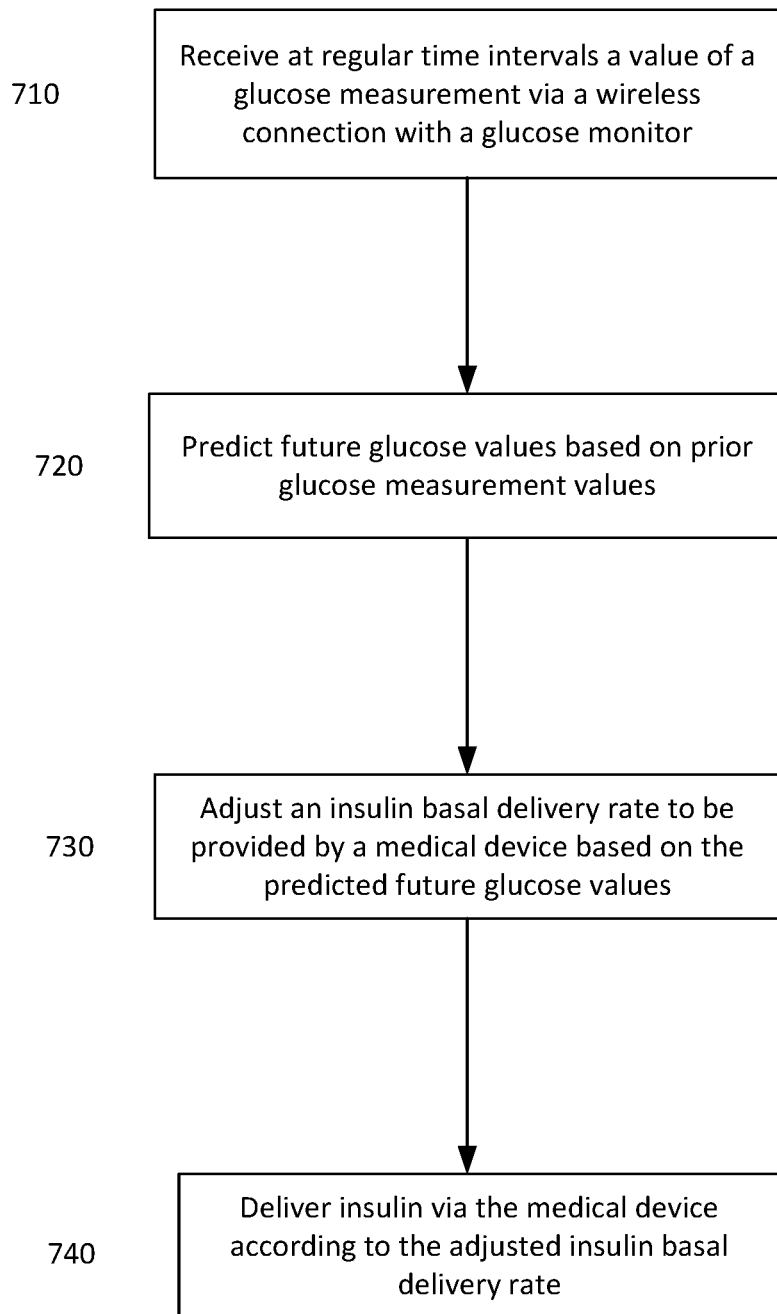
FIG. 7A shows a flow chart of a process utilizing predicted future glucose values to adjust an insulin basal delivery according to examples described herein.

It may be helpful to briefly describe an operational example performed by system 100 with reference to FIG. 7A. The AP algorithm 169 or 129 of FIG. 1 executing on a management device processor 161 or 121 of FIG. 1 may implement process 700 as shown in FIG. 7A. At 710, the AP algorithm may receive at regular time intervals a glucose measurement via a wireless connection (e.g., 108 or 112) with a glucose monitor (such as sensor 104). Regular time intervals may be intervals, such as approximately every 5 minutes, 10 minutes, hourly, a particular time(s) of day, or the like. Based on the prior glucose values, the AP algorithm may predict future glucose values (720). Based on the predicted future glucose values from 720, the AP algorithm may, at 730, adjust insulin delivery, for example, by adjusting an insulin basal delivery rate, based on predicted future glucose values. At 740, insulin may be delivered via the medical device according to the adjusted insulin basal delivery rate. For example, the medical device 102 can deliver an amount of insulin to the user at regular time periods, such as approximately every 5 minutes or the like, with the amount adjusted based on received glucose values.

The process 700 of the example of FIG. 7A may continue with the processor receiving a subsequent glucose measurement value via the wireless connection with the glucose monitor. The total daily insulin-based basal glucose level may be determined using the received subsequent glucose measurement value and the prior glucose values from a past time period. The processor may compare the total daily insulin-based basal glucose level to a user-set basal glucose setpoint (e.g., 110-120 mg/dL or the like). In response to a result of the comparison indicating the user-set basal glucose setpoint is erroneous, the processor may determine an updated insulin basal delivery rate to be delivered by the medical device. In the example, the updated insulin basal delivery rate is updated from the adjusted insulin basal delivery rate from step 730.

Techniques described herein provide safety constraints for the delivery of insulin based on known or unknown failures or inaccuracies of the sensor 104. Various operational scenarios and examples of response thereto by the system 100 are described herein.

In an operational example, the system 100 may react with an automatic suspension of insulin deliver when a blood glucose measurement id below a glucose threshold according to the following discussion. In the operational example, regardless of predictions made by the AP algorithm, the AP algorithm can enter an automatic suspension mode when a glucose level determined by the sensor 104 is below a threshold (e.g., below 60 mg/dL). The AP algorithm can automatically resume delivering insulin based on model prediction control (MPC) algorithms when glucose values rise above the threshold. In various examples, when hypoglycemia is detected (e.g., based on glucose levels being below a predetermined threshold), the drug delivery system 100 can stop delivery of insulin to the user. Automatically resuming delivery to the user can be provided when the glucose levels rise above the threshold. MPC algorithms—operating as part of the AP algorithm—can be used for automatic start-up.

Figure 6:
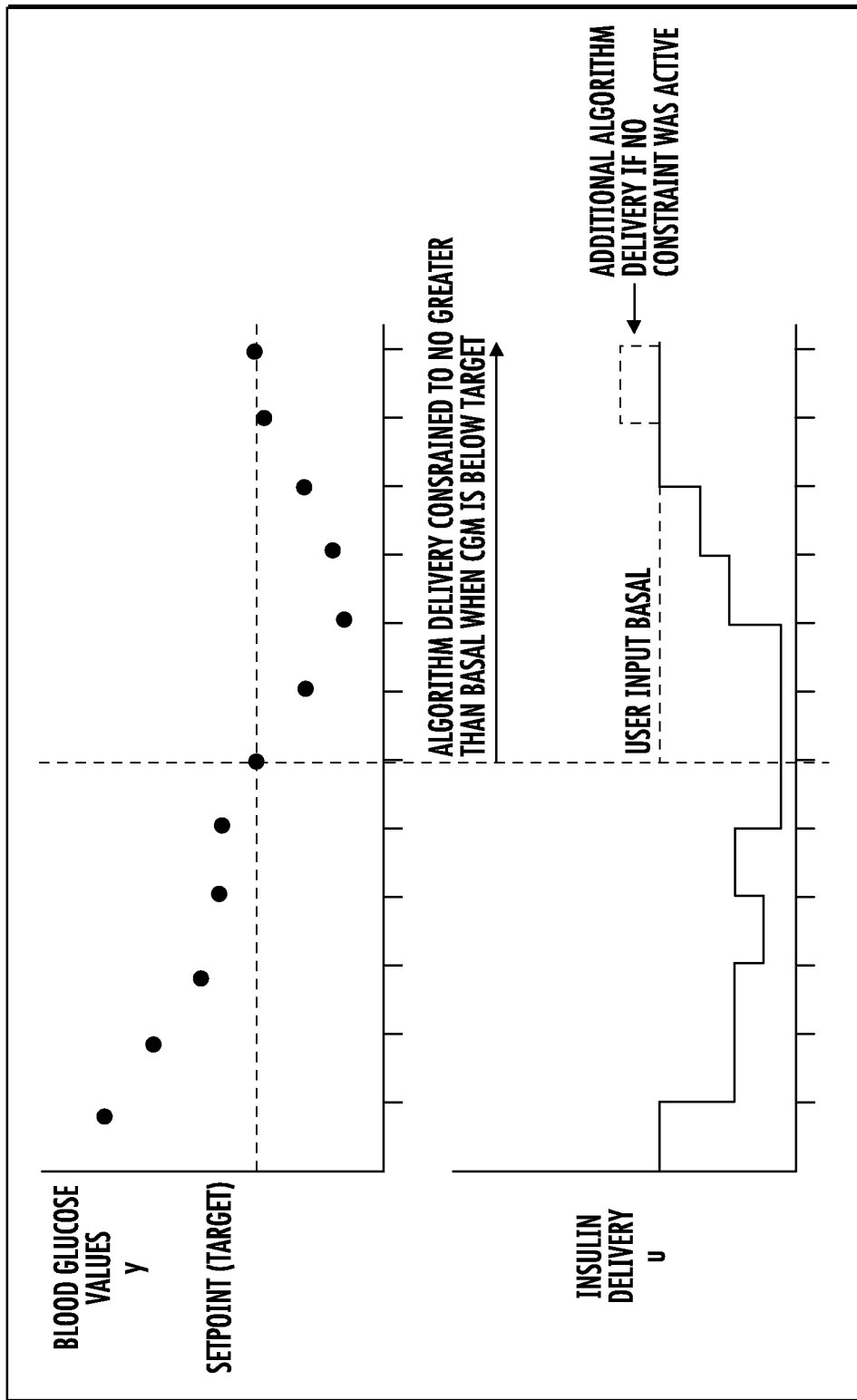
FIG. 6 illustrates an example of constraining insulin delivery to no more than a fixed rate of insulin when glucose values are below a predetermined threshold.

In other operational examples, the system 100 may react with to constrain the AP algorithm to a basal below a threshold according to the following discussion. In various examples, the AP algorithm can be constrained to deliver no more than a fixed rate of insulin when glucose values are below a predetermined threshold. FIG. 6 illustrates an example of constraining delivery to no more than a fixed rate of insulin under such a scenario. The AP algorithm may attenuate or suspend insulin delivery when glucose values are below the threshold. The fixed rate of insulin delivery can be personalized to the user and can be determined by the user's entered basal rate, a rate calculated by the AP algorithm-based on average AP algorithm-based daily delivery, a rate based on the user's weight, age, total daily insulin (TDI), and/or other metrics.

As an example, a "TDI-based basal" can be calculated by multiplying the user's total daily insulin requirement, or the sum of insulin deliveries of the user for a past time period, such as 24 hours, by 0.5 (assuming that the basal would naturally be covered by half of the user's total insulin requirements per day, while the other half of the user's total insulin requirements per day is covered by insulin provided at meal time, or as a bolus), then dividing that value by 24 (i.e. number of hours in a day). For instance, if the user's TDI is 48, the user's TDI-based basal is 48*0.5/24, or 1 U/h. This gives an estimate of the total basal the user may actually need, daily, with reduced susceptibility to any erroneously user-entered basal values.

Figure 2:
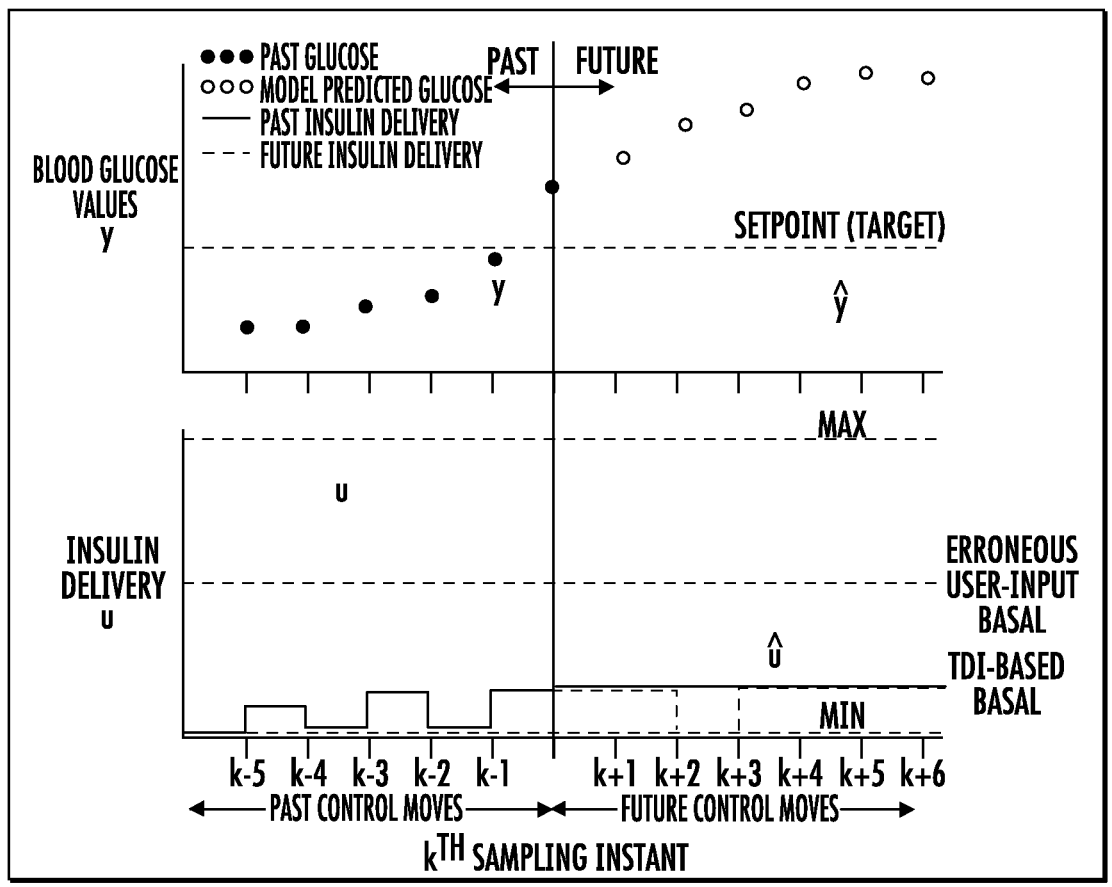
FIG. 2 illustrates an example of the fixed rate of insulin delivery for a user being roughly limited to the user's TDI-based insulin.

The predetermined threshold may be a fixed (e.g., hard wired) threshold, a user set threshold, or a user set threshold adjusted by a fixed (positive or negative) deviation value (e.g., the user set target glucose less a fixed 10 mg/dL adjustment). As an example, the fixed rate of insulin delivery can be roughly half of a set basal delivery when glucose levels are below the predetermined threshold. FIG. 2 illustrates an example of the fixed rate of insulin delivery for a user being roughly limited to the user's TDI-based insulin.

Techniques described herein can account for sensor values provided to the AP algorithm/the drug delivery system 100 that may be incorrect or erroneous for any number of reasons by providing sensor independent safety constraints. In such instances, the system 100 may implement a glucose independent safety constraint for maximum delivery of insulin over a period of time as described below.

For example, FIG. 8 shows a flow chart of a process for implementing an example of a safety constraint in response to an over-delivery of insulin. In various examples, such as in process 800, the AP algorithm can be constrained to a maximum fixed rate of insulin delivery if the AP algorithm has delivered more than a preset volume of insulin, personalized to the user, over a set amount of time. For example, a process is operable to upon execution of an AP algorithm to deliver a maximum amount of the user's entered basal or TDI based basal if the AP algorithm has delivered 3 times the sum of the user's basal delivery in the past 3 hours—often referred to as the 3×3 rule). The processor (such as processor 161) coupled to a medical device (such as 102, which may be a pump) may determine that the medical device has delivered more than a preset volume of insulin over a set amount of time (810). An amount of insulin to be delivered by the medical device as an adjusted basal dosage may be adjusted based on a calculation using a volume of insulin delivered over the set amount of time and a total daily insulin to be delivered as calculated by an artificial pancreas algorithm (820). At 830, the processor may limit the amount of insulin to be delivered as the adjusted basal dosage to a maximum volume of a user's basal insulin delivery volume divided by either a time increment, at which the adjusted basal dosage is administered or a percentage of an hourly basal rate. In the example of FIG. 8, the time increment may be at regular time intervals. Examples of regular time intervals may be less than an hour, such as for example, 5 minutes, 9 minutes, 23 minutes or the like, longer than an hour, or the like. Alternatively, the time increments may simply be increments that are based on a counter value or the like.

Figure 5:
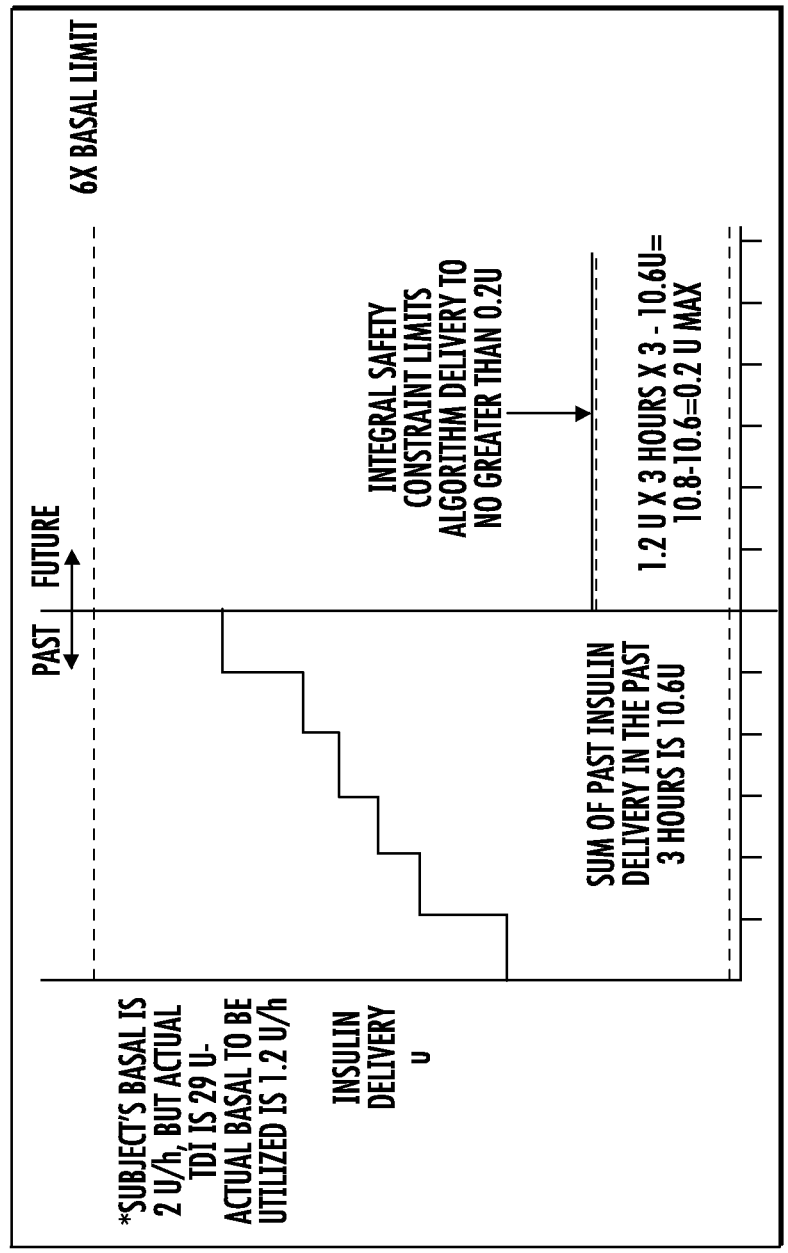
FIG. 5 illustrates an example of constraining maximum insulin delivery.

The AP algorithm may attenuate or suspend insulin delivery in this case but is constrained to a maximum insulin delivery. FIG. 5 illustrates an example of constraining maximum insulin delivery. The fixed rate of insulin delivery and the preset volume of insulin delivery can be personalized to the user and can be determined by the user's entered basal rate, a rate calculated by the AP algorithm-based on average AP algorithm-based daily delivery, a rate based on weight, age, total daily insulin delivered, total daily basal delivered, or other metrics. Additionally, the constrained delivery may be accompanied by an alert or alarm to the user indicating the same.

In other instances, the system 100 may implement a glucose independent safety constraint for maximum delivery of insulin at one time as described below. In various examples, the AP algorithm can be constrained to deliver no more than a fixed volume of insulin personalized to the user over any one control cycle. For example, the AP algorithm can deliver no more than 6 times the user's basal divided in 5-minute increments (e.g., often referred to as the 6× rule), or 50% of the hourly basal rate in one algorithm delivery (e.g., basal rate of 1.2 u/hr/2=0.6 units). The fixed volume of insulin delivery can be personalized to the user and can be determined by the user's entered basal rate, a rate calculated by the AP algorithm-based on average AP algorithm-based daily delivery, a rate based on weight, age, total daily insulin delivered, total daily basal delivered, or other metrics.

In further instances, the system 100 may implement a glucose independent safety constraint to limit under delivery of insulin as described below. In various examples, the AP algorithm/the drug delivery system 100 can implement a negative insulin on board (JOB) constraint. The AP algorithm can enter a fixed rate of insulin delivery mode personalized to the user if the AP algorithm under-delivers insulin by more than a volume of insulin personalized to the user over a period of time incorporating the JOB. For example, 2.5 times the user's basal in the past 4 hours, after applying an IOB decay curve. The AP algorithm calculates the remaining IOB at each control cycle. A negative IOB determination can indicate that the algorithm has been delivering below a fixed personalized rate (i.e., basal) for a period of time of insulin delivery history. The negative IOB value can be the cumulative "under basal" delivery accounting for IOB decay.

FIG. 9 illustrates a flow chart of a process for implementing an example of a safety constraint in response to an under-delivery of insulin. In the process 905, a processor (such as 121 or 161 of FIG. 1) may receive signals from a medical device indicative of an amount of insulin being delivered by the medical device (such as 102 of FIG. 1), the processor may maintain a total amount (e.g., volume) of insulin delivered as, for example, an insulin delivery history, in a memory (such as 123 or 163 of FIG. 1). The insulin delivery history may, for example, span minutes, hours, days, weeks, months, a time period between doctor appointments, years, or the like. In the example process 905, a processor of a medical management device (such as 106 of FIG. 1) may determine in response to receipt of a glucose measurement value from a sensor (such as 104 of FIG. 1) that a medical device has been delivering insulin below a fixed personalized basal rate for a period of time of insulin delivery history (915). A result of delivering insulin below a fixed personalized basal rate is a negative insulin on board value. At 925, the processor may determine that the negative insulin on board value is greater than three times a user's total daily insulin-based hourly basal value. In response to the negative insulin on board value being greater than a multiple (such as 3, 6, 2.5 or the like) of a user's total daily insulin-based hourly basal value, delivery of insulin by the medical device may be altered to deliver a total daily-based basal or a personalized volume of insulin (935). At 945, a notification message may be output requesting the user to acknowledge the altered delivery of insulin or a requirement for a new calibration value for use by the processor in calculating a calibrated amount of insulin for delivery.

The process 905 may continue at 955 the process 905 determines whether a user acknowledgment of request for a new calibration value has been received. In response to receipt of user acknowledgement of the altered delivery of insulin, the medical device continues the altered delivery of insulin (962). In response to receipt of the new calibration value, the processor generates the new calibration value (965) and the new calibration value is applied by the processor to calculate the calibrated amount of insulin for delivery (975).

In various examples, if this negative IOB determination is greater than 3 times the user's TDI-based hourly basal value, the AP algorithm can revert to delivering the TDI-based basal or personalized volume of insulin and inform the user of the same. User input can be required via a notification message for the user to acknowledge the system state or requirement for a new calibration value. The system 100 can deliver basal until the notification message is acknowledged or the calibration entered. Further, the system 100 can resume operating in a manner prior to the negative IOB determination in response to a user acknowledgement and/or performance of a calibration of sensor 104, which in this example, may be a continuous glucose monitor (CGM).

Disclosed are examples that relate to determining and resolving communication issues, such as those between any of a sensor, such as 104, and a pump 102 and/or a management device, such as 106 in a drug delivery system, such as that described with reference to FIG. 1.

Figure 7B:
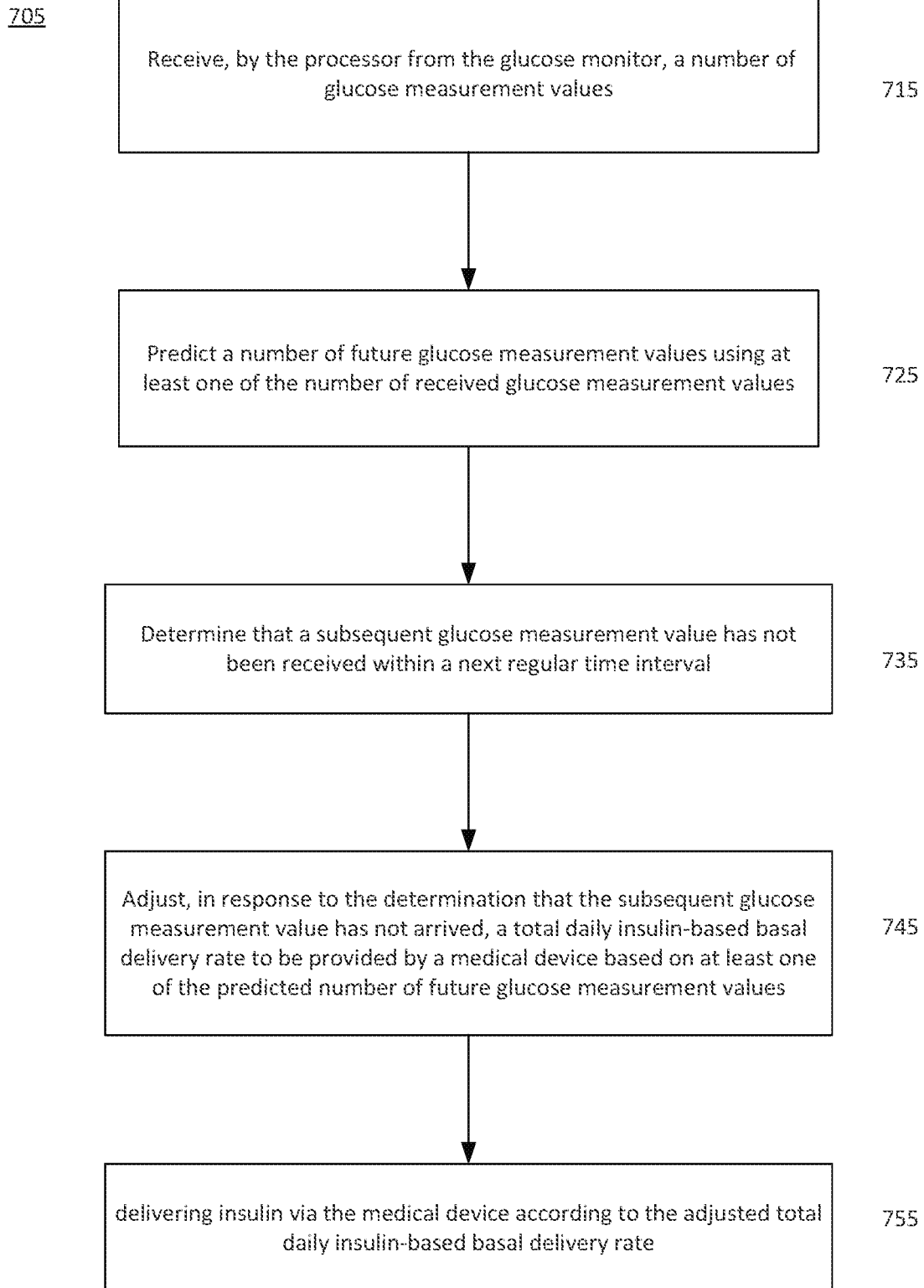
FIG. 7B shows a flow chart of a process for implementing an example of a safety constraint in response to a communication issue within a drug delivery system such as the example drug delivery system shown in FIG. 1.

FIG. 7B shows a flow chart of a process for implementing an example of a safety constraint in response to a communication issue within a drug delivery system such as the example drug delivery system shown in FIG. 1. In various examples, under a scenario where measurement values from the sensor 104 are not being received by the AP algorithm (e.g., missing values from the sensor 104), the system 100 may respond according to the example process 705 shown in FIG. 7B. In the example of FIG. 7B, the process 705 may be a response based on the last known value (or values) from the sensor 104. For example, at 715, a processor, such as 121, 141, or 161, may receive a number of glucose measurement values from the sensor 104. In the example, each glucose measurement value of the number of glucose measurement values may be received at a regular time interval over a period of time and the regular time interval is less than the period of time. of course, the regular time intervals may be like those mentioned in the discussion of FIG. 7A. The processor may use at least one of the number of received glucose measurement values, at 725, to predict future glucose values. For example, each time the AP algorithm executing on the processor receives a value, a future glucose value to be received at a future time interval may be predicted. The processor may determine that a subsequent glucose measurement value has not been received within a next regular time interval (735). For example, when a glucose measurement value from the sensor 104 is expected but not received, the system 100 can use the predicted glucose values generated when the last received value from the sensor 104 was received. For example, in response to the determination that the subsequent glucose measurement value has not arrived, a total daily insulin-based basal delivery rate may be adjusted to be provided by a medical device based on at least one of the predicted number of future predicted glucose values (745). The processor may issue instructions to the medical device, such as 102 of FIG. 2, so insulin, at 755, may be delivered via the medical device 102 according to the adjusted total daily insulin-based basal delivery rate.

In a further example, the insulin may be delivered via the medical device according to the adjusted total daily insulin-based basal delivery rate for a trusted prediction period of time. In the further example, the processor may further determine to suspend delivery of insulin in response to a last-received glucose measurement value being within a particular range of previous glucose measurement values and the trusted prediction period of time spanned a duration of time corresponding to a predetermined number of regular time intervals. The time period during which delivery of insulin is to be suspended may be determined based on a value of the last-received glucose measurement value falling within a particular range of a plurality of ranges of glucose measurement values. In response, a time period for suspending the delivery of insulin may be selected from a number of pre-set time periods, and the processor may suspend deliver of insulin for the selected time period.

Alternatively, the medical device may deliver the insulin using the prior predicted future glucose values (and corresponding insulin dosage values) for an allowed "trusted prediction" period of time. In yet another example, the insulin delivery can continue if the last received value from the sensor 104 was above a threshold and is predicted to deliver above a baseline rate of insulin, and predictions can be used for 15 minutes or longer.

If the values from the sensor 104 do not resume before the trusted prediction period of time ends, then the AP algorithm response may depend on the last received value (or values) from the sensor 104 and the predictions based thereon by the AP algorithm. In various examples, the AP algorithm can respond with insulin delivery and possibly a notification to the user via the management device 106, for example, according to the following table:

| Loss of signal when last valid value from CGM sensor meets the following condition | System/AP/Algorithm response | System/AP/Algorithm response (extended bolus) | Notification to the user (after consecutive missing points) |
| --- | --- | --- | --- |
| CGM value > Setpoint - 10 | Trust prediction for 3 missing estimated glucose values (EGVs). Afterwards, if still missing values or communication from the sensor:<br>1. If AP algorithm recommended suspension for all three cycles, suspend basal for 20 minutes, then resume basal.<br>2. If AP algorithm recommended two or less suspensions during these three cycles, resume basal. | Continue delivering extended bolus for 3 points. If still missing communication from the sensor:<br>1. If AP algorithm recommended delivery below the new basal for all three cycles, revert to basal without extended portion for 1 hour.<br>2. If AP algorithm recommended delivery below the new basal for two or less suspensions during these three cycles, continue extended bolus. | Notify the user of missing points after 1 hour. |
| Setpoint – 10 ≥ CGM value > 70 | Trust prediction for 3 missing EGVs. Afterwards, if still missing values or communication from the sensor:<br>1. If AP algorithm recommended two or more suspensions during these three cycles, suspend basal for 20 minutes, then resume basal.<br>2. If AP algorithm recommended one or 0 suspensions during these three cycles, resume basal. | Continue delivering extended bolus for 3 points. If still missing communication from the sensor:<br>1. If AP algorithm recommended delivery below the new basal for two or more cycles, revert to basal without extended portion for 1 hour.<br>2. If AP algorithm recommended delivery below the new basal for one or 0 cycles during these three cycles, continue extended bolus. | Notify the user of missing points after 1 hour. |
| 70 ≥ CGM value > 60 | Trust prediction for 3 missing EGVs. Afterwards, if still missing values or communication from the sensor:<br>1. If AP algorithm recommended any suspensions during these three cycles, suspend basal for 45 minutes, then resume basal. | Continue delivering extended bolus for 3 points. If still missing communication from the sensor:<br>1. If AP algorithm recommended delivery below the new basal for any cycle, revert to original basal. | Notify the user of missing points after 1 hour. |

-continued

| Loss of signal when last valid value from CGM sensor meets the following condition | System/AP/Algorithm response | System/AP/Algorithm response (extended bolus) | Notification to the user (after consecutive missing points) |
|---|---|---|---|
| | 2. If AP algorithm delivered any amount above zero for all three cycles, resume basal. | 2. If AP algorithm recommended delivery at or above the new basal for all three cycles, continue extended bolus. | |
| 60 ≥ CGM value | Suspend for 60 minutes in closed loop and then resume basal. | Revert to basal without extended portion until new CGM value. | Notify the user of missing points after 1 hour. |

In various examples, each cycle (e.g., control cycle) referred to above can be of any duration including, but not limited to, approximately 5 minutes, 8 minutes or the like.

In various examples, the AP algorithm may permanently or temporarily attenuate the extended portion of an extended bolus in response to glucose level alone, glucose level and AP algorithm predictions, or AP algorithm predictions alone. In various examples, the AP algorithm may automatically cancel an extended portion of an extended bolus in response to glucose levels alone, glucose levels and AP algorithm predictions, or AP algorithm predictions alone. The extended portion of the extended bolus may be applied to correction or meal IOB for future automated or manual insulin dosing decisions. If applied to correction IOB, the AP algorithm may be more conservative in low glycemia. If applied to correction IOB, the AP algorithm may be more conservative in high glycemia.

In other instances, the system 100 may limit the system's response to a hypoglycemic event response such as ingesting rescue carbohydrates as described below. For example, in the case where the user experiences a hypoglycemic event (e.g., glucose concentration is below a 70 mg/dL hypoglycemic threshold), the user may act by ingesting fast acting carbohydrates to quickly increase the user's blood glucose. This is an unannounced meal to the system 100 which has the potential to be viewed by the system 100 as a very rapid increase in glucose. In response, the system 100 may respond by delivering additional insulin to compensate for these carbohydrates. However, this may not be a preferred response as the carbohydrates were taken specifically to increase the glucose levels of the user and the user may not want to receive insulin to counteract these carbohydrates.

In an example, the processor, by executing programming code stored in a memory, may perform a function to determine, based on a measurement provided by a glucose monitor (such as sensor 104 of FIG. 1), a hypoglycemic event has occurred. In response to the determination a hypoglycemic event has occurred, the system 100 via a processor, such as 121, 141 or 161, may update the adjusted insulin basal rate. For example, the processor may update the adjusted insulin basal rate by setting a reduced temporary basal rate of the medical device that is used for dosing calculations for a predetermined period of time following the determination of the occurrence of the hypoglycemic event. Alternatively, the system 100 via a processor may set a reduced temporary basal rate that may be used in dosing calculations until a glucose rate of change decreases below a predetermined threshold after the determination of the occurrence of the hypoglycemic event. In another alternative, the system 100 may set a reduced temporary basal rate that can be used in dosing calculations until the blood glucose (a measured by a sensor, such as 104 of FIG. 1) is above a predetermined threshold following the determination of the occurrence of the hypoglycemic event.

For example, techniques for detecting such a scenario (e.g., the system 100 detecting an ingestion of fast acting carbohydrates to address a hypoglycemic event) are described herein and may include the following detection techniques: 1) Detection of a rapid rate of increase in glucose concentrations beyond a certain threshold (e.g., 2 mg/dL per minute); 2) Detection of a rapid rate of increase in glucose concentration across a certain series of glucose concentration values when the first value of the series is below a first threshold (e.g., detecting a rapid rate of change as in (1) when the first value of the series is below the hypoglycemic threshold of 70 mg/dL); 3) Detection of a rapid rate of increase in glucose concentration when any value of the series is below a second threshold (e.g., detecting a rapid rate of change as in (1) when any value in the series is below the system target glucose of 120 mg/dL); and/or 4) Detection of a rapid change in the second derivative (e.g., acceleration) of the glucose concentration higher than a predetermined threshold (e.g., finding a significant change in the rate of change of glucose concentrations across any number of points—e.g., from a glucose concentration decrease of 2 mg/dL per minute to an increase of 2 mg/dL per minute).

Figure 10:
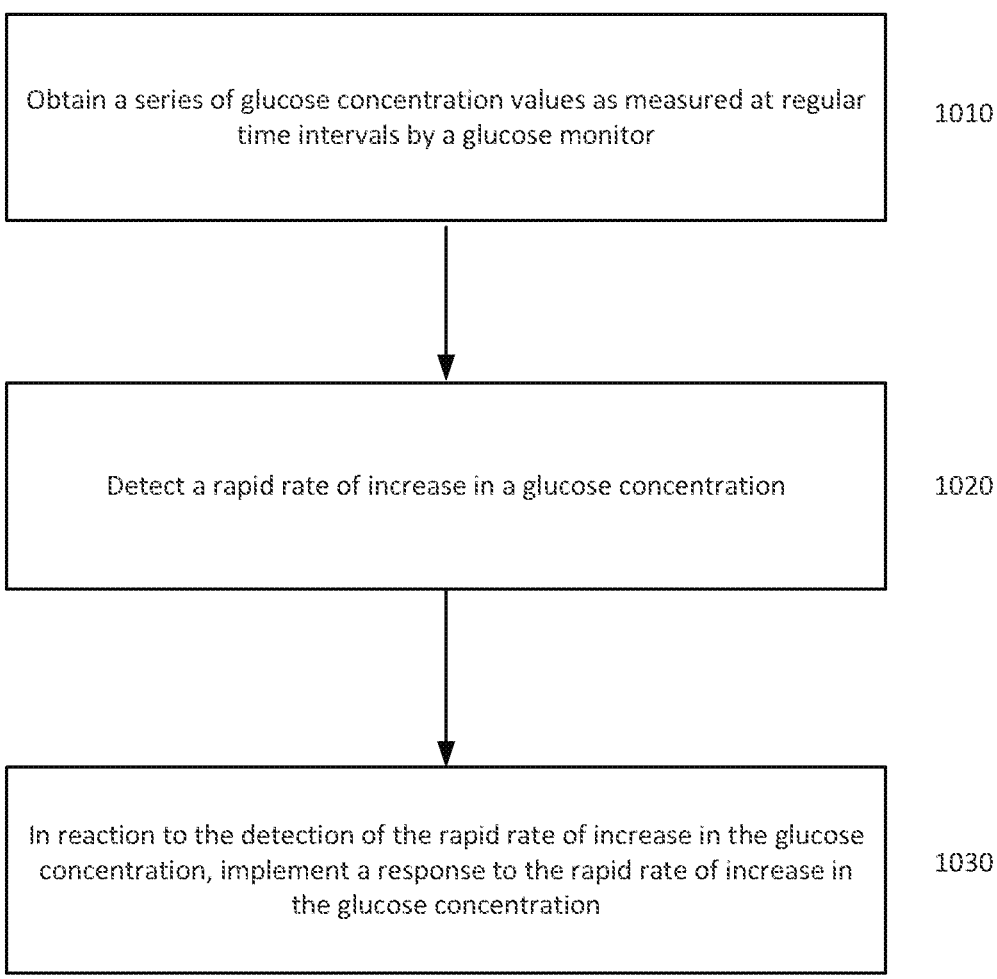
FIG. 10 shows a flow chart of a process example for implementing an example of a response to the rapid rate of increase in the glucose concentration.

FIG. 10 is a flowchart of an example process for implementing an example of a response to a rapid rate of increase in glucose concentration, or measurements. In the example of FIG. 10, a processor executing programming code, such as an AP algorithm, may perform a process 1000. The processor may be operable to obtain a series of glucose concentration values as measured at regular time intervals by a glucose monitor (1010). The processor may detect a rapid rate of increase in a glucose concentration and may implement a response to the rapid rate of increase in the glucose concentration in reaction to the detection of the rapid rate of increase in the glucose concentration, or measurements (1020).

Figure 4:
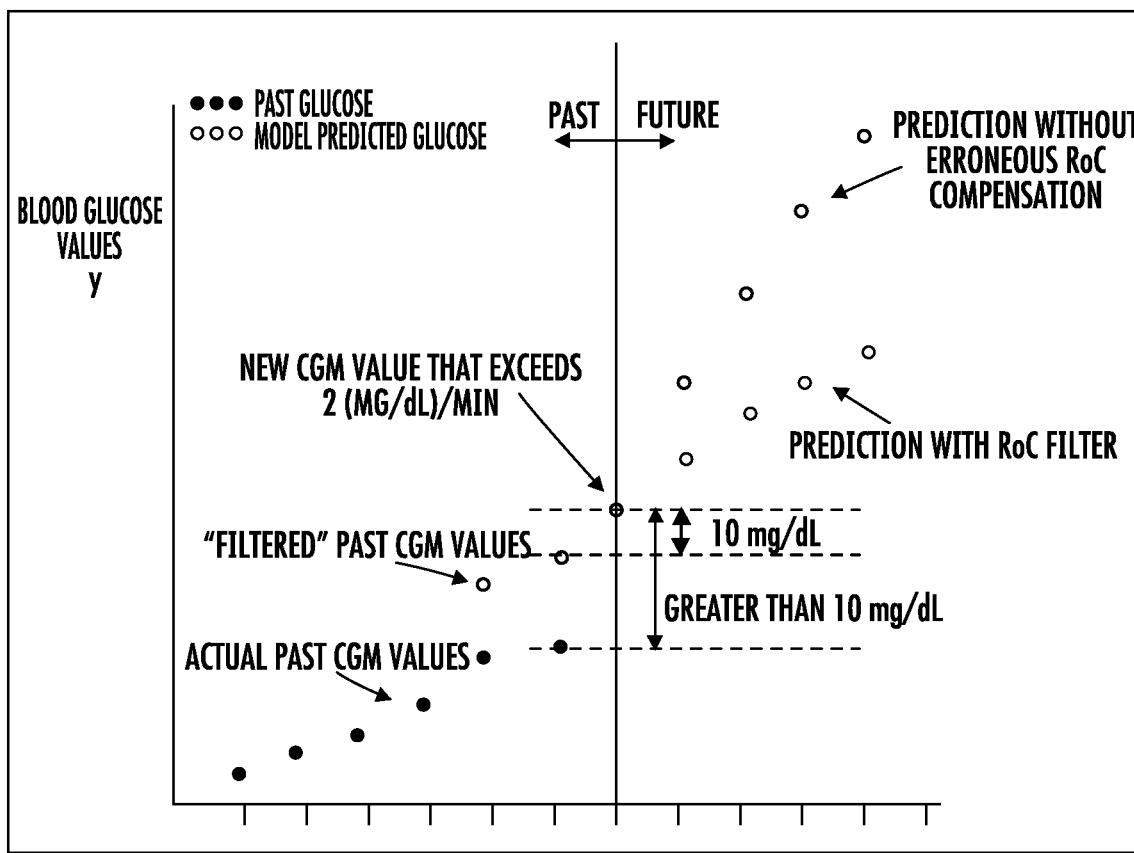
FIG. 4 illustrates an example of effects of a rate of change filter to blood glucose value predictions made by an example of an artificial pancreas algorithm intended to lower an estimated trajectory of future blood glucose values.

For example, in response to detecting (using, for example, the above the detection techniques) a rapid rate of increase in glucose concentration that is indicative of the ingestion of fast acting carbohydrates to address a hypoglycemic event, a response to detection of the ingestion of fast acting carbohydrates to address a hypoglycemic event (e.g., by the system 100) may be implemented (1030). In an example, a processor within system 100, upon executing the programming code, may be operable to perform functions when implementing a response to the rapid rate of increase in the glucose concentration such as those described below. Examples of techniques implemented by the system via the processor executing programming code may implement a response the detection of the ingestion of fast acting carbohydrates (based on the rapid rate of increase in glucose concentration) in response to the rapid rate of increase in the glucose concentration are described below and may include one or more of the following:

i. Limit the AP algorithm recommended delivery to a delivery maximum personalized to the user (e.g., no greater than basal) for a specified duration of time (e.g., 25 minutes) after the event.

ii. Limit the AP algorithm recommended delivery to a delivery maximum personalized to the user (e.g., no greater than basal) until a rate of change decreases below a predetermined threshold after a hypoglycemic event.

iii. Limit the AP algorithm recommended delivery to a delivery maximum personalized to the user (e.g., no greater than basal) until the glucose is above a predetermined threshold after a hypoglycemic event.

iv. Limit the AP algorithm delivery of insulin with any combination of techniques i., ii., or iii.

v. Reduce the AP algorithm gain, cost function, and/or aggressiveness for a predetermined period of time after the hypoglycemic event. The AP algorithm gain, for example, may be the model gain, which is an indication of how much a user's glucose will change per unit of insulin. A cost function may, for example, be a measure of the excursion of the glucose error value from the set point. The set point may be, for example, a target glucose value (e.g., 113 mg/dL), which may be, in the example, a setting within a range of approximately 110-120 mg/dL, or the like. In general, the further away a glucose measurement value is (either higher or lower) from the target glucose value, the higher the cost value generated by the cost function, while a glucose measurement value closer to the target glucose value has a lower cost value. In an example, the cost function may be related to deviations in the measured glucose and expected glucose and/or deviations in an expected amount of insulin and the basal insulin amount. Aggressive may be related to the responsiveness of the AP algorithm to deviations in the cost function. Aggressiveness may be viewed as how quickly the AP algorithm aims to reduce the cost function and drive the glucose measurement value to the set point. A high aggressive setting may attempt to drive the glucose measurement value to the set point quickly, while a low aggressive setting may correct the glucose value more smoothly.

vi. Reduce the AP algorithm gain, cost function, and/or aggressiveness until the glucose is above a predetermined threshold after a hypoglycemic event.

vii. Reduce the AP algorithm gain, cost function, and/or aggressiveness until the rate of change decreases below a predetermined threshold after a hypoglycemic event.

viii. Limit the AP algorithm delivery of insulin with any combination of techniques v, vi, or vii.

ix. Implement a glucose rate of change filter for a predetermined period of time following a hypoglycemic event. FIG. 4 illustrates an example of how the rate of change filter can affect the predictions made by the AP algorithm to result in a lower estimate trajectory of future blood glucose values. A rate of change filter may be used by a processor executing the AP algorithm (such as processor 121, 141 or 161) to limit the rate of change of glucose that is seen (acted upon) by, or provided to, the AP algorithm. For example, glucose measurement values may be provided by a glucose sensor. Using multiple glucose measurement values, a rate of change of the glucose measurement values may be determined. The rate of change filter may be used to either attenuate or amplify the rate of change of glucose measurement values utilized by the AP algorithm. Application of the rate of change filter may, for example, be limited for a duration of time from when the processor determines the glucose measurement value first went below a predetermined threshold or from a time that the glucose comes above a predetermined threshold after being triggered. For example, if the rate of change is high (e.g., 4 mg/dL) following rescue carbohydrate ingestion, the rate of change filter can limit the rate of change seen by the algorithm to 2 mg/dL for 30 minutes after coming back above 70 mg/dL to reduce the AP algorithm response to the carbohydrates.

x. Implement a glucose rate of change filter following a hypoglycemic event until the rate of change decreases below a predetermined threshold.

xi. Implement a glucose rate of change filter following a hypoglycemic event until the glucose is above a predetermined threshold.

xii. Implement a glucose rate of change filter at all times.

xiii. The rate of change filter may be for both positive and negative rate of change or a positive rate of change only.

xiv. Implement a glucose rate of change filter using any combination of techniques ix, x, xi, xii, or xiii.

xv. The system 100 can set a reduced target blood glucose value that can be used for dosing calculations for a predetermined period of time following a hypoglycemic event.

xvi. The system 100 can set a reduced target blood glucose value that can be used for dosing calculations until a glucose rate of change decreases below a predetermined threshold after a hypoglycemic event.

xvii. The system 100 can set a reduced target blood glucose value that can be used for dosing calculations until the glucose is above a predetermined threshold.

xviii. The system 100 can set a reduced target blood glucose value for any combination of techniques xv, xvi, or xvii above.

All aforementioned predetermined thresholds may be user-defined, fixed, adapted over time using AP algorithm parameters, or personalized to the user based on TDI or a TDI derivative. In addition, other responses, such as reducing a temporary basal rate that is used for dosing calculations are described in more detail with reference to other examples.

Returning to the system example of FIG. 1, the management device processor 161 of management device 106 in the system 100 may be operable, upon execution of the programming instructions including the artificial pancreas algorithm, to perform various functions. For example, the management device processor may determine times and dosages of insulin to be delivered to a user. The times and the dosages may be calculated based on a user's sex, a user's age, a user's weight, a user's height, and/or on glucose levels provided by the sensor.

In an example, the management device processor 161 may determine an occurrence of a hypoglycemic event. In response to the determination of the occurrence of the hypoglycemic event, the management device processor may implement a glucose rate of change filter for a predetermined period of time. The glucose rate of change filter may limit a rate of change in measured blood glucose values used by the artificial pancreas algorithm in the determination of a time for delivery of insulin and a dosage of the insulin being delivered. The management device processor may instruct the medical device via wireless link 110 to deliver the determined dosage of the insulin at the determined time for delivery. The management device processor 161 may limit a duration of time for implementation of the glucose rate of change filter by applying one or more limitations, including: a time when a measured glucose value first went below a predetermined threshold related to the hypoglycemic event, from a time that a measured glucose value comes above another predetermined threshold after the occurrence of the hypoglycemic event, until the glucose rate of change decreases below a further predetermined threshold, or until the glucose is above an additional predetermined threshold.

The management device processor 161 may be further operable to apply the glucose rate of change filter at one of: at all times, when both a positive and a negative glucose rate of change are determined, or only when a positive glucose rate of change is determined.

In another example, the management device processor 161 upon execution of the artificial pancreas algorithm is further operable to perform one of: change from closed loop operation modes to open loop operation mode; constrain a maximum insulin delivery according to a basal delivery rate personalized for a user for a set period of time after detection or until an event is over, wherein the event is an event different from the hypoglycemic event; deliver a set personalized basal rate for a set period of time after detection or until the hypoglycemic event is over; limit the rate of change as used by the processor for a set period of time after detection or until the event is over; or the rate of change filter is applied to limit the response by the artificial pancreas algorithm at all times or following a hypoglycemic event.

In some scenarios, insulin delivery may not be attenuated as rapidly as desired (e.g., at a rate suitable to recover), for example, in case of the occurrence of, or the impending occurrence of, a hypoglycemic event. For example, the system 100 may attenuate insulin delivery at or below the quantity of insulin the user may receive without the system 100 if the user's glucose value is below a threshold or is trending to being reduced below a threshold. However, there may be a risk that the system 100 may not attenuate insulin delivery as rapidly as desired, leading the processor, for example, to cause the medical device to deliver insulin even when the user has an impending hypoglycemic risk. FIG. 11 shows a flow chart of a process example for implementing an example of a response that increases a likelihood of suspension of insulin. In the process 1100, for example, a processor coupled to a glucose sensor in the system 100 may determine insulin delivery is not attenuating at rate suitable to recover from a hypoglycemic event or an impending hypoglycemic event (1110). In response, the processor may apply safety constraints to further reduce insulin.

For example, the processor may address this slower attenuation utilizing the foregoing techniques that modify the processor reaction via the AP algorithm and the described safety constraints executed by the processor. At 1120, the processor may address such a scenario in the following manner:

a. In various examples, calculations made by the artificial pancreas algorithm may increase the likelihood of suspension of insulin by reducing the penalty of estimated outcomes where the insulin delivery request is below a user-inputted basal delivery; or b. In various examples, calculations made by the artificial pancreas algorithm may increase the likelihood of suspension of insulin by scaling the deviations of insulin delivery below the user input basal to be proportional to the user-inputted basal delivery.

In other examples, the system 100 may manage other scenarios in which insulin delivery is not being attenuated during exercise or other activity that may induce increased hypoglycemic risk using a number of techniques. For example, the system 100 can attenuate insulin delivery when an external disturbance to the system 100 such as exercise or an activity causes reduction in glucose concentrations and increase in hypoglycemic risk. The system 100 may automatically detect this external disturbance. Alternatively, the external disturbance may be announced or indicated to the system 100 by a user (e.g., through a user interface on the medical device 102 and/or the management device 106 (not shown)). FIG. 12 is a flow chart of a process example for implementing an example of a response that attenuates insulin delivery. In the example process 1200, a processor coupled to a glucose sensor in the system 100 may determine insulin delivery is not attenuating at rate suitable to maintain glucose concentrations (1210) or mitigate a hypoglycemic event or an impending hypoglycemic event. In response, the processor may apply safety constraints to further reduce insulin. For example, the processor may alter either a control target glucose value by increasing the control target (i.e., glucose setpoint) to a glucose value higher than the current target (e.g., to 150 mg/dL or the like from a lower current target). Alternatively, the system 100 may reduce an input basal value to a value lower than a current input basal value (e.g., approximately 25% of the user's input basal)(1220). In various examples, the system 100 may be subject to an additional upper bound in insulin delivery (e.g., the system 100 may not request insulin delivery greater than approximately 75% of the user's input basal). As a result of the application of the safety constraints, attenuating insulin delivery at a more rapid rate to maintain glucose concentrations (1230).

In some examples, the system 100 may not have sufficient insulin history related to the user. In response, insulin delivery history data and glucose value history data can be used by the system 100 to operate effectively within a closed loop mode of operation. If there is no known insulin history when in closed loop mode, then there may be a risk that the user has IOB and the AP algorithm may deliver more insulin than necessary. Techniques herein can address such a scenario where the system 100 may not have sufficient historical operating data.

In various examples, if the system 100 does not have sufficient glucose history when starting closed loop operation, the system 100 may respond in one of the following ways:

I. Prompt the user with a query of whether non-basal insulin was delivered in a previous duration of time. If the answer is yes, limit the AP algorithm maximum delivery of insulin to a predetermined value for a set amount of time (e.g., limit delivery to 1.5 times the user's basal for 2 hours);

II. Request a user response to a query of whether a non-basal insulin dose was delivered within a previous duration of time. If the answer is yes (i.e., an affirmative response), have the user enter in the amount of insulin delivered and optionally also the time it was taken. Using this information, the user's IOB can be calculated and provided to the AP algorithm to safely deliver insulin. The IOB may be used by a predictive algorithm or directly limit the amount of insulin to be delivered while the IOB remains; or III. Limit the maximum delivery by the AP algorithm to a predetermined value (such as for example 100-120 mg/dL) for a set amount of time if there is not sufficient insulin history when starting into closed loop mode.

Returning to the system example of FIG. 1, the management device processor 161 of the management device 106 may upon execution of the artificial pancreas algorithm may be operable to perform additional functions.

For example, the management device processor 161 may determine, upon starting closed loop operation of the artificial pancreas algorithm, that sufficient glucose history is unavailable (i.e., the glucose history is insufficient) for use by the artificial pancreas algorithm. In response to the determination sufficient glucose history is unavailable, the management device processor may request the user enter into the management device an amount of insulin delivered. The request may also include a request for a time when, or an estimated elapsed time since, the insulin was delivered. In response to receiving an amount of insulin delivered, a user's insulin on board may be calculated based on the amount of insulin delivered. Optionally, if the time when the insulin was delivered or the estimated elapsed time since the insulin was delivered is provided, these respective time or elapsed time may be included in the calculation. For example, the management device processor may be operable to determine elapsed time if only the time when the insulin was delivered is provided. The management device processor may use the calculated user's insulin on board to determine utilizing a user-personalized insulin decay curve when the user's calculated insulin on board is to fall below a predetermined threshold. Alternatively, the management device processor may, in response to the determination sufficient glucose history is unavailable, either limit maximum delivery of insulin to a predetermined value for a set amount of time or request a user response to a query of whether a non-basal insulin dose was delivered within a previous duration of time.

In some examples, the AP algorithm/system setpoint changes in response to various inputs or events (e.g., exercise or eating a meal). The system 100 can operate to maintain a user at a specific target, or setpoint (e.g., desired glucose level). In various examples, the system 100 may allow the user to set or change the setpoint of the system 100 under certain scenarios or for certain instances. In various examples, the system 100 may allow the user to set or change the setpoint of the system 100 temporarily for a user defined amount of time, after expiration of which the system 100 can revert to the previous target.

In various examples, the setpoint may be defined as a profile with different setpoints being set for different time segments of the day. The target blood glucose level may change automatically at each time segment. In various examples, in the case of a setpoint change, the system 100 may respond abruptly to the step change and deliver too much or too little insulin. To prevent the system 100 from responding to the step change, the prediction by the AP algorithm can be shifted by the amount of the target change. This can prevent the prediction from being impacted by the step change in target.

Figure 3:
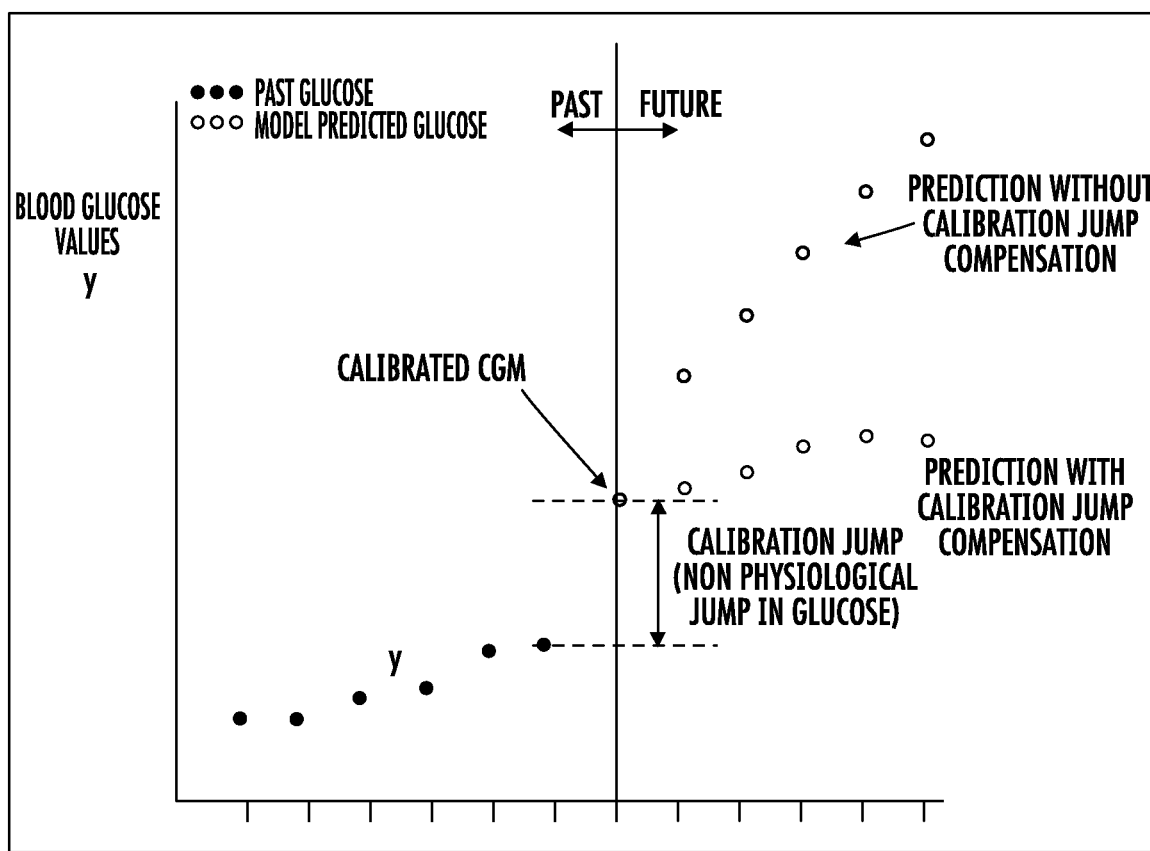
FIG. 3 illustrates an example of adjusting a prediction trajectory based on a new glucose measurement value.

In some examples, safety constraints implemented via the AP algorithm may enable the AP algorithm to respond to sensor aberrations—noise and value step changes—such as those represented in FIG. 3. For example, techniques that enable the system 100 to effectively manage responses to aberrations of the sensor 104 or abrupt step changes that are non-physiological. For example, non-physiological aberrations of the sensor 104 may be caused by a noisy sensor 104 or by a physical interaction with the sensor 104 such as putting pressure on the sensor 104 or by bumping or hitting the sensor 104. The system 100 may respond to this sudden change in value from the sensor 104 and errantly deliver a drug. Techniques described herein can address this undesirable response and enable such events to be detected by the system 100 in the following ways: A) by determining a sensor value trend only, B) by determining a sensor value trend in one direction followed by an opposite trend—detecting a sudden change in trend, C) by determining a rate of change of the sensor value, and/or D) by determining that a first derivative or other filtering may be used. In addition, or as alternative E), in some examples, data obtained from an accelerometer within the sensor, such as 104, may be used in combination with the trend. For example, pressure induced sensor issues can occur at higher rates, for example, when a person is sleeping so sleep detection via the accelerometer data may also be used to enhance the detection of the incident. The accelerometer data may also be used to sense impact to the sensor or delivery unit to enhance the detection. For example, a processor may process the accelerometer data to detect the sleep or an orientation of a person when the sensor experiences a pressure induced sensor issue.

In various examples, upon detection of any of the above listed events A-E, the system 100 may respond in any of the following ways: AA) The AP algorithm may change modes such as changing from closed loop operation to open loop operation; BB) Constrain the system 100 to a maximum delivery personalized to the user (e.g., basal) for a set period of time after detection or until the event (i.e., one of listed events A-E above) is over; CC) Deliver a set personalized rate (e.g., basal rate) for a set period of time after detection or until the event is over; DD) The AP algorithm may limit the rate of change as used by the system 100 for a set period of time after detection or until the event is over, or EE) A rate of change filter may be implemented to limit the response by the AP algorithm at all times or following a hypoglycemic event.

Safety constraints as applied to the AP algorithm and executed by a processor in system 100 may control system responses to sensor calibrations, particularly when the sensor is a continuous glucose monitor. For example, under certain situations where sensor calibrations may be required, there may be a resulting step change in a sensor value. In response, the system 100 may deliver a drug in response to such a step change. For example, the current state of the system 100 upon which a prediction can be based can depend on the input sensor values at each control step. These sensor values can be dependent on user-input reference calibration values (e.g., finger-sticks), and may change significantly if there is a significant discrepancy between the sensor readings and the finger-stick values used for calibration.

These rapid changes in sensor values can introduce an artificial step-change in the glucose trajectory (e.g., a calibration jump as shown in FIG. 3) that is not a true reflection of the actual trends in the glucose concentrations. Further, the existence of a significant discrepancy between finger-stick blood glucose (BG) values and CGM values at the time of calibration means that CGM values that were input to the system 100 prior to the calibration reference input, as well as the state estimation due to those CGM values, are less reliable and may not reflect the current state. Therefore, when these events are detected, the AP algorithm's prediction "trajectory" is reset to a flat value that matches the current, new CGM value. FIG. 3 illustrates an example of adjusting a prediction trajectory based on a new CGM value.

In various examples, this reinitialization may be implemented for positive and negative step changes. In various examples, this reinitialization may be limited to positive step change in the blood glucose values due to calibration only, as a negative step change in blood glucose values may induce a reduction or suspension in insulin delivery for a few cycles which may be acceptable.

For example, in system 100 of FIG. 1, a processor, such as 121, 141 or 161, may be operable to execute a process by which the processor receives one or more glucose measurement values from the glucose monitor, such as sensor 104.

The processor may also receive a user-input reference calibration value. Using the one or more glucose values and the user-input reference calibration value, the processor may identify a discrepancy between the one or more glucose values from the glucose monitor and the user-input reference calibration value. Based on the identified discrepancy, the processor may modify the adjusted insulin basal delivery rate.

In some examples, prior to modifying the adjusted insulin basal delivery rate based on the identified discrepancy, the processor may calibrate the glucose monitor based on the identified discrepancy. The processor may further determine the identified discrepancy is a positive step change in an amount of insulin being delivered. A positive step change may be, for example, an increase in a delivered amount of insulin. In response to the identified discrepancy being a positive step change, the processor may obtain a current, new blood glucose measurement value from the calibrated glucose monitor. After obtaining the current new blood glucose measurement value, the processor may use the current, new blood glucose value to modify the adjusted insulin basal delivery rate based on the identified discrepancy. Alternatively, the identified discrepancy may be determined to be a negative step change, which is a decrease in a delivered amount of insulin. In response to the identified discrepancy being a negative step change, the processor may provide an instruction to suspend delivery of insulin for a predetermined amount of time prior to modifying the adjusted insulin basal delivery rate based on the identified discrepancy.

The techniques described herein for providing safety constraints for a drug delivery system (e.g., the system 100 or any component thereof) can be implemented in hardware, software, or any combination thereof. For example, the system 100 or any component thereof can be implemented in hardware, software, or any combination thereof. Software related implementations of the techniques described herein can include, but are not limited to, firmware, application specific software, or any other type of computer readable instructions that can be executed by one or more processors. Hardware related implementations of the techniques described herein can include, but are not limited to, integrated circuits (ICs), application specific ICs (ASICs), field programmable arrays (FPGAs), and/or programmable logic devices (PLDs). In some embodiments, the techniques described herein, and/or any system or constituent component described herein can be implemented with a processor executing computer readable instructions stored on one or more memory components.

Some embodiments of the disclosed device may be implemented, for example, using a storage medium, a computer-readable medium or an article of manufacture which may store an instruction or a set of instructions that, if executed by a machine (i.e., processor or microcontroller), may cause the machine to perform a method and/or operation in accordance with embodiments of the disclosure. Such a machine may include, for example, any suitable processing platform, computing platform, computing device, processing device, computing system, processing system, computer, processor, or the like, and may be implemented using any suitable combination of hardware and/or software. The computer-readable medium or article may include, for example, any suitable type of memory unit, memory device, memory article, memory medium, storage device, storage article, storage medium and/or storage unit, for example, memory (including non-transitory memory), removable or non-removable media, erasable or non-erasable media, writeable or re-writeable media, digital or analog media, hard disk, floppy disk, Compact Disk Read Only Memory (CD-ROM), Compact Disk Recordable (CD-R), Compact Disk Rewriteable (CD-RW), optical disk, magnetic media, magneto-optical media, removable memory cards or disks, various types of Digital Versatile Disk (DVD), a tape, a cassette, or the like. The instructions may include any suitable type of code, such as source code, compiled code, interpreted code, executable code, static code, dynamic code, encrypted code, programming code, and the like, implemented using any suitable high-level, low-level, object-oriented, visual, compiled and/or interpreted programming language. The non-transitory computer readable medium embodied programming code may cause a processor when executing the programming code to perform functions, such as those described herein.

Certain examples, or embodiments, of the present disclosure were described above. It is, however, expressly noted that the present disclosure is not limited to those embodiments, but rather the intention is that additions and modifications to what was expressly described herein are also included within the scope of the disclosed examples. Moreover, it is to be understood that the features of the various examples described herein were not mutually exclusive and can exist in various combinations and permutations, even if such combinations or permutations were not made express herein, without departing from the spirit and scope of the disclosed examples. In fact, variations, modifications, and other implementations of what was described herein will occur to those of ordinary skill in the art without departing from the spirit and the scope of the disclosed examples. As such, the disclosed examples are not to be defined only by the preceding illustrative description.

What is claimed is:

1. A non-transitory computer readable medium embodied with programming code executable by a processor, and the processor when executing the programming code is operable to perform functions, including functions to:
   receive, at regular time intervals, a value of a glucose measurement made by a glucose monitor;
   predict future glucose values based on prior glucose measurement values;
   adjust an insulin basal delivery rate to be provided by a medical device based on the predicted future glucose values;
   identify a discrepancy between one or more glucose measurement values received from the glucose monitor and a user-input reference calibration value;
   modify the adjusted insulin basal delivery rate based on the identified discrepancy; and
   deliver insulin via the medical device according to the modified, adjusted insulin basal delivery rate.

2. The non-transitory computer readable medium of claim 1, wherein the programming code when executed by the processor, the processor performs further functions to:
   receive a subsequent glucose measurement value via the wireless connection with the glucose monitor;
   determine a total daily insulin-based basal glucose level using the received subsequent glucose measurement value and the prior glucose values from a past time period;
   compare the total daily insulin-based basal glucose level to a user-set basal glucose setpoint; and
   in response to a result of the comparison indicating the user-set basal glucose setpoint is erroneous, determine an updated insulin basal delivery rate to be delivered by the medical device, wherein the updated insulin basal delivery rate is updated from the adjusted insulin basal delivery rate.

3. The non-transitory computer readable medium of claim 1, wherein the programming code when executed by the processor, the processor performs further functions to:
receive one or more glucose measurement values from the glucose monitor; and
receive the user-input reference calibration value.

4. The non-transitory computer readable medium of claim 3, wherein the programming code when executed by the processor, the processor prior to modifying the adjusted insulin basal delivery rate based on the identified discrepancy, performs further functions to:
calibrate the glucose monitor based on the identified discrepancy;
determine the identified discrepancy is a positive step change in an amount of insulin being delivered, wherein the positive step change is an increase in a delivered amount of insulin;
in response to the identified discrepancy being a positive step change, obtain a current, new blood glucose measurement value from the calibrated glucose monitor; and
use the current, new blood glucose measurement value to update the adjusted insulin basal delivery rate based on the identified discrepancy.

5. The non-transitory computer readable medium of claim 3, wherein the programming code when executed by the processor, the processor prior to modifying the adjusted insulin basal delivery rate based on the identified discrepancy, performs further functions to:
calibrate the glucose monitor based on the identified discrepancy;
determining the identified discrepancy is a negative step change, wherein the negative step change is a decrease in a delivered amount of insulin; and
in response to the identified discrepancy being a negative step change, provide an instruction to suspend delivery of insulin for a predetermined amount of time.

6. The non-transitory computer readable medium of claim 1, wherein the programming code when executed by the processor, the processor performs further functions to:
determine, based on a measurement provided by the glucose monitor, a hypoglycemic event has occurred; and
update the adjusted insulin basal delivery rate in response to the determination that a hypoglycemic event has occurred.

7. The non-transitory computer readable medium of claim 6, wherein the programming code when executed by the processor, the processor, when updating the adjusted insulin basal delivery rate in response to the determination that a hypoglycemic event has occurred, performs further functions to:
set a reduced temporary basal delivery rate of the medical device that is used in dosing calculations for a predetermined period of time following the determination of the occurrence of the hypoglycemic event.

8. The non-transitory computer readable medium of claim 6, wherein the programming code when executed by the processor, the processor, when updating the adjusted insulin basal delivery rate in response to the determination that a hypoglycemic event has occurred, performs further functions to:
set a reduced temporary basal delivery rate of the medical device that is used in dosing calculations until a rate of change of blood glucose levels decreases below a predetermined threshold following the determination of the occurrence of the hypoglycemic event.

9. The non-transitory computer readable medium of claim 6, wherein the programming code when executed by the processor, the processor, when updating the adjusted insulin basal delivery rate in response to the determination that a hypoglycemic event has occurred, performs further functions to:
set a reduced temporary basal delivery rate of the medical device that is used in dosing calculations until a blood glucose level is above a predetermined threshold following the determination of the occurrence of the hypoglycemic event.

10. A method performed by a processor coupled to a glucose monitor and a medical device via wireless connections, the method comprising:
receiving, by the processor from the glucose monitor, a number of glucose measurement values, wherein each glucose measurement value of the number of glucose measurement values is received at a regular time interval over a period of time and the regular time interval is less than the period of time;
predicting a number of predicted future glucose values using at least one of the number of glucose measurement values;
determining that a subsequent glucose measurement value has not been received within a next regular time interval;
in response to the determination that the subsequent glucose measurement value has not arrived, adjusting a total daily insulin-based basal delivery rate to be provided by a medical device based on at least one of the number of predicted future glucose values; and
delivering insulin via the medical device according to the adjusted total daily insulin-based basal delivery rate, wherein the insulin is delivered via the medical device according to the adjusted total daily insulin-based basal delivery rate for a trusted prediction period of time.

11. The method of claim 10, further comprising:
in response to a last-received glucose measurement value being within a particular range of previous glucose measurement values and the trusted prediction period of time spanned a duration of time corresponding to a predetermined number of regular time intervals, determining delivery of insulin is to be suspended;
based on a value of the last-received glucose measurement value falling within a particular range of a plurality of ranges of glucose measurement values, selecting a time period for suspending the delivery of insulin from a plurality of pre-set time periods; and
suspending deliver of insulin for the selected time period.

12. The method of claim 10, further comprising:
determining, by the processor, that the medical device has delivered more than a preset volume of insulin over a set amount of time, wherein the preset volume of insulin is based on one or more of: a user input basal rate, a rate calculated by an artificial pancreas algorithm using an average daily delivery rate, a rate based on user weight and/or user age, a total daily insulin delivered, or a total daily basal delivered; and
in response to the determination, adjusting an amount of insulin to be delivered by the medical device as an adjusted basal dosage based on a calculation using a volume of insulin delivered over the set amount of time and a total daily insulin to be delivered as calculated by an artificial pancreas algorithm.

13. The method of claim 12, further comprising:
limiting the amount of insulin to be delivered as the adjusted basal dosage to a maximum volume of a user's basal insulin delivery volume divided by either a time increment at which the adjusted basal dosage is administered or a percentage of an hourly basal rate, wherein the time increment is less than an hour.

14. A system, comprising:
a medical device comprising a pump, a reservoir configured to contain insulin, a processor and a transceiver, wherein the medical device is operable to deliver insulin in response to outputs from the processor;
a sensor comprising a transmitter, a processor and a cannula, the sensor operable to measure blood glucose and output a blood glucose value; and
a management device comprising a management device processor, a management device memory configured to store programming instructions including an artificial pancreas algorithm, and a management device transceiver, wherein the management device processor is operable upon execution of the programming instructions including the artificial pancreas algorithm to:
determine an occurrence of a hypoglycemic event;
in response to the determination of the occurrence of the hypoglycemic event, implement a glucose rate of change filter for a predetermined period of time, wherein the glucose rate of change filter limits a rate of change in measured blood glucose values used by the artificial pancreas algorithm in a determination of a time for delivery of insulin and a dosage of the insulin to be delivered; and
instruct the medical device to deliver a determined dosage of the insulin at a determined time for delivery.

15. The system of claim 14, wherein the processor of the management device upon execution of the artificial pancreas algorithm is further operable to:
limit a duration of time for implementation of the glucose rate of change
filter by applying one or more limitations from:
a time when a measured glucose value first went below a predetermined threshold related to the hypoglycemic event,
a time that a measured glucose value is above another predetermined threshold after the occurrence of the hypoglycemic event,
until the glucose rate of change decreases below a further predetermined threshold, or
until the glucose is above an additional predetermined threshold.

16. The system of claim 14, wherein the management device processor, upon execution of the artificial pancreas algorithm, in addition to after the determination of the occurrence of the hypoglycemic event, implements the glucose rate of change filter at one of: at all times, when both a positive and a negative glucose rate of change are determined, or only when a positive glucose rate of change is determined.

17. The system of claim 14, wherein the processor of the management device upon execution of the artificial pancreas algorithm is further operable to:
determine times and dosages of insulin to be delivered to a user, wherein the times and the dosages are calculated based on a user's sex, a user's age, a user's weight, a user's height, and/or on glucose levels provided by the sensor.

18. The system of claim 14, wherein the processor of the management device upon execution of the artificial pancreas algorithm is further operable to perform one of:
change from closed loop operation modes to open loop operation mode;
constrain a maximum insulin delivery according to a basal delivery rate personalized for a user for a set period of time after detection or until an event is over, wherein the event is different from the hypoglycemic event;
deliver a set personalized basal rate for a set period of time after detection or until the hypoglycemic event is over;
limit the rate of change as used by the processor for a set period of time after detection or until the event is over; or
the glucose rate of change filter is applied to limit the response by the artificial pancreas algorithm at all times or following a hypoglycemic event.

19. The system of claim 14, wherein the processor of the management device upon execution of the artificial pancreas algorithm is further operable to:
determine, upon starting closed loop operation of the artificial pancreas algorithm, that sufficient glucose history is unavailable for use by the artificial pancreas algorithm; and
in response to the determination that sufficient glucose history is unavailable, either:
limit maximum delivery of insulin to a predetermined value for a set amount of time; or
request a user response to a query of whether a non-basal insulin dose was delivered within a previous duration of time.

20. The system of claim 14, wherein the processor of the management device upon execution of the artificial pancreas algorithm is further operable to:
determine, upon starting closed loop operation of the artificial pancreas algorithm, that sufficient glucose history is unavailable for use by the artificial pancreas algorithm;
in response to the determination that sufficient glucose history is unavailable, request a user enter provide the management device with an amount of insulin delivered by a medical device;
in response to receiving an amount of insulin delivered in response to the request, calculate a user's insulin on board based on the amount of insulin delivered; and
use the calculated user's insulin on board to determine utilizing a user-personalized insulin decay curve when the user's calculated insulin on board is to fall below a predetermined threshold.

* * * * *